(12) United States Patent
Kim

(10) Patent No.: US 11,666,607 B2
(45) Date of Patent: Jun. 6, 2023

(54) **NANOVESICLES DERIVED FROM *FAECALIBACTERIUM PRAUSNITZII* AND USES THEREOF**

(71) Applicant: MD HEALTHCARE INC., Seoul (KR)

(72) Inventor: Yoon-Keun Kim, Paju-si (KR)

(73) Assignee: MD HEALTHCARE INC., Seoul (KR)

( * ) Notice: Subject to any disclaimer, the term of this patent is extended or adjusted under 35 U.S.C. 154(b) by 57 days.

(21) Appl. No.: 15/733,371

(22) PCT Filed: Jan. 10, 2019

(86) PCT No.: PCT/KR2019/000368
§ 371 (c)(1),
(2) Date: Jul. 11, 2020

(87) PCT Pub. No.: WO2019/139360
PCT Pub. Date: Jul. 18, 2019

(65) Prior Publication Data
US 2021/0093677 A1    Apr. 1, 2021

(30) Foreign Application Priority Data

Jan. 12, 2018 (KR) .................. 10-2018-0004604
Jan. 9, 2019 (KR) .................. 10-2019-0002607

(51) Int. Cl.
| | | |
|---|---|---|
| *A61K 35/74* | (2015.01) | |
| *A61P 9/10* | (2006.01) | |
| *C12Q 1/689* | (2018.01) | |
| *A61P 9/06* | (2006.01) | |
| *A61P 25/16* | (2006.01) | |
| *A61P 35/00* | (2006.01) | |
| *A61K 9/127* | (2006.01) | |

(52) U.S. Cl.
CPC .............. *A61K 35/74* (2013.01); *A61K 9/127* (2013.01); *A61P 9/06* (2018.01); *A61P 9/10* (2018.01); *A61P 25/16* (2018.01); *A61P 35/00* (2018.01); *C12Q 1/689* (2013.01)

(58) Field of Classification Search
None
See application file for complete search history.

(56) References Cited

U.S. PATENT DOCUMENTS 9,066,971 B2 * 6/2015 Gho ................. A61K 9/5068

FOREIGN PATENT DOCUMENTS

| CN | 105120847 A | 12/2015 | |
|---|---|---|---|
| CN | 106687119 A | 5/2017 | |
| CN | 107429290 A | 12/2017 | |
| EP | 3 012 270 A1 | 4/2016 | |
| JP | 2017-508464 A | 3/2017 | |
| KR | 10-2015-0134356 A | 12/2015 | |
| KR | 10-2017-0015958 A | 2/2017 | |
| WO | 2011/096809 A1 | 8/2011 | |
| WO | 2014/102009 A1 | 7/2014 | |
| WO | 2016/063263 A2 | 4/2016 | |
| WO | 2016/133324 A1 | 8/2016 | |
| WO | 2016/172657 A2 | 10/2016 | |
| WO | WO-2017152137 A2 * | 9/2017 | ........ A23L 29/065 |
| WO | 2018/008895 A1 | 1/2018 | |
| WO | 2018/124606 A1 | 7/2018 | |

OTHER PUBLICATIONS

Jafari et al., "Isolation and characterization of Faecalibacterium prausnitzii extracellular vesicles", Vaccine Research, 2017, vol. 4, No. 3-4, pp. 51-54.
Chinese Office Action for corresponding CN application 201980007976.2, dated Nov. 26, 2021, 9 pages.
Jafari et al., "Isolation and characterization of Faecalibacterium prausnitzii extracellular vesicles." Vaccine Research, 2017, vol. 4(3), pp. 51-54.
Lopez-Siles et al., "Changes in the Abundance of Faecalibacterium rausnitzii Phylogroups I and II in the Intestinal Mucosa of Inflammatory Bowel Disease and Patients with Colorectal Cancer", Inflamm. Bowel Dis., 2016, vol. 22(1), pp. 28-41.
Extended European Search Report dated Sep. 9, 2021, in corresponding EP Application No. 19738195.7, 10 pages.
Notice of Reasons for Refusal (Office Action) dated Aug. 13, 2021, in corresponding JP Application No. 2020-538572, 13 pages, with English translation.
Jafari et al., "Isolation and characterization of Faecalibacterium prausnitzii extracellular vesicles", Vaccine Research, 2017, vol. 4, No. 3, pp. 51-54.

(Continued)

*Primary Examiner* — Celeste A Roney
(74) *Attorney, Agent, or Firm* — Vorys, Sater, Seymour and Pease LLP; Mih Suhn Koh

(57) ABSTRACT

Provided are vesicles derived from *Faecalibacterium prausnitzii* and to uses thereof. It has been experimentally confirmed by the present inventors that the vesicles in the clinical samples of patients with gastric cancer, colorectal cancer, liver cancer, pancreatic cancer, cholangiocarcinoma, ovarian cancer, bladder cancer, lymphoma, myocardial infarction, atrial fibrillation, and Parkinson's disease were significantly reduced in comparison with a normal person and that when vesicles isolated from the strain were administered, the secretion of inflammatory mediators caused by pathogenic vesicles, such as *E. coli*-derived vesicles, was significantly inhibited. The vesicles derived from *Faecalibacterium prausnitzii* according to the subject matter are expected to be usefully employed for the purposes of developing a method for diagnosing gastric cancer, colorectal cancer, liver cancer, pancreatic cancer, cholangiocarcinoma, ovarian cancer, bladder cancer, lymphoma, myocardial infarction, atrial fibrillation, and/or Parkinson's disease, and a composition for preventing, alleviating, or treating said diseases.

4 Claims, 17 Drawing Sheets

Specification includes a Sequence Listing.

(56) References Cited

OTHER PUBLICATIONS

Korenori et al., "Current status and problems of 16S rRNA pyrosequencing-based profiling of gastro-intestinal microbiota", Japanese Journal of Lactic Acid Bacteria, 2012, vol. 23, No. 1, pp. 24-34.

Martin et al., "Functional Characterization of Novel Faecalibacterium prausnitzii Strains Isolated from Healthy Volunteers: A Step Forward in the Use of F. prausnitzii as a Next-Generation Probiotic", Frontiers in Microbiology, 2017, vol. 8, 13 pages.

Munukka et al., "Faecalibacterium prausnitzii treatment improves hepatic health and reduces adipose tissue inflammation in high-fat fed mice", The ISME Journal, 2017, vol. 11, No. 7, pp. 1667-1679.

* cited by examiner

NANOVESICLES DERIVED FROM *FAECALIBACTERIUM PRAUSNITZII* AND USES THEREOF

CROSS-REFERENCE TO RELATED APPLICATIONS

This application is a 371 of PCT/KR2019/000368, filed Jan. 10, 2019, which claims the benefit of priority from Korean Patent Application No. 10-2018-0004604, filed Jan. 12, 2018 and Korean Patent Application No. 10-2019-0002607, filed Jan. 9, 2019, the contents of each of which are incorporated herein by reference in its entirety.

SEQUENCE LISTING

The Sequence Listing submitted in text format (.txt) filed on Jul. 11, 2020, named "SequenceListing.txt", created on Jun. 3, 2020 (750 bytes), is incorporated herein by reference.

TECHNICAL FIELD

The present invention relates to *Faecalibacterium prausnitzii*-derived nanovesicles and the use thereof, and more particularly, to a method of diagnosing gastric cancer, colorectal cancer, liver cancer, pancreatic cancer, cholangiocarcinoma, ovarian cancer, bladder cancer, lymphoma, myocardial infarction, atrial fibrillation and Parkinson's disease using *Faecalibacterium prausnitzii*-derived nanovesicles, and a composition for preventing, alleviating or treating the above-mentioned disease, which includes the above-mentioned vesicles.

BACKGROUND ART

Since the beginning of the 21st century, acute infectious diseases recognized as epidemic diseases in the past have become less important, whereas chronic inflammatory diseases accompanied by immune dysfunction caused by disharmony between humans and microbiomes have changed disease patterns as main diseases that determine the quality of life and the human lifespan. As an intractable chronic inflammatory disease in the 21st century, cancer, cardiovascular diseases, chronic lung diseases, metabolic diseases, and neuropsychiatric diseases have become a big problem for public health in the country as main diseases that determine the human lifespan and the quality of life.

It is known that the number of microorganisms coexisting in the human body has reached 100 trillion, which is 10 times more than the number of human cells, and the number of microorganism genes is more than 100 times the number of human genes. A microbiota or microbiome refers to a microbial community including bacteria, archaea and eukarya present in a given habitat.

Bacteria coexisting in our body and bacteria present in the ambient environment secrete nanometer-sized vesicles in order to exchange information on genes, low molecular compounds, proteins, and the like with other cells. The mucosa forms a physical defense membrane through which particles having a size of 200 nanometers (nm) or more cannot pass, so that bacteria coexisting in the mucosa cannot pass through the mucosa, but vesicles derived from bacteria have a size of 100 nanometers or less and are absorbed into our bodies after relatively freely passing through epithelial cells via the mucosa. Bacteria-derived vesicles that are locally secreted from bacteria are absorbed via epithelial cells of the mucous membrane to thereby induce a local inflammatory response, and the vesicles having passed through the epithelial cells are systematically absorbed via lymphatic vessels and thereby distributed in respective organs, and immune and inflammatory responses are regulated in the organs in which the vesicles are distributed. For example, vesicles derived from pathogenic gram-negative bacteria such as *Escherichia coli* locally cause colitis, and promote a systemic inflammatory response, stool and blood coagulation through a vascular endothelial inflammatory response when absorbed into blood vessels, and cause insulin resistance and diabetes when absorbed into insulin-acting muscle cells. On the other hand, vesicles derived from beneficial bacteria may control a disease by controlling immune dysfunction and metabolic dysfunction caused by pathogenic vesicles.

As immune responses to factors such as bacteria-derived vesicles, Th17 immune responses characterized by the secretion of the interleukin (hereinafter, IL)-17 cytokine occur, and IL-6 is secreted when exposed to bacteria-derived vesicles, thereby inducing Th17 immune responses. Inflammation caused by the Th17 immune response is characterized by neutrophil infiltration, and during the process by which inflammation occurs, tumor necrosis factor-alpha (hereinafter, TNF-α) secreted from inflammatory cells such as neutrophils and macrophages plays an important role in inflammation and oncogenesis.

*Faecalibacterium prausnitzii* is a gram-positive bacterium that coexists in the human large intestine, and is known as a bacterium fermenting dietary fiber to produce short-chain fatty acids such as butyrate. When the bacteria decrease in number, it was reported to be associated with Crohn's disease, obesity, asthma, and depression. However, the fact that *Faecalibacterium prausnitzii* extracellularly releases vesicles has not been reported so far, and particularly, no case in which *Faecalibacterium prausnitzii* is applied to the diagnosis and treatment of cancer or intractable diseases such as cardiovascular-brain diseases has been reported.

Thus, in the present invention, it was confirmed that a disease could be diagnosed by confirming that vesicles derived from *Faecalibacterium prausnitzii* were significantly decreased in clinical samples of patients with gastric cancer, colorectal cancer, liver cancer, pancreatic cancer, cholangiocarcinoma, ovarian cancer, bladder cancer, lymphoma, myocardial infarction, atrial fibrillation and Parkinson's disease compared to normal individuals. Further, as a result of isolating vesicles from *Faecalibacterium prausnitzii* and analyzing characteristics thereof, it was confirmed that the vesicles could be used as a composition for preventing or treating a disease such as gastric cancer, colorectal cancer, liver cancer, pancreatic cancer, cholangiocarcinoma, ovarian cancer, bladder cancer, lymphoma, myocardial infarction, atrial fibrillation and Parkinson's disease.

DISCLOSURE

Technical Problem

To address the above-described problems, as a result of having conducted intensive research, the inventors of the present invention confirmed through metagenomic analysis that the content of vesicles derived from *Faecalibacterium prausnitzii* was significantly reduced in samples derived from patients with gastric cancer, colorectal cancer, liver cancer, pancreatic cancer, cholangiocarcinoma, ovarian cancer, bladder cancer, lymphoma, myocardial infarction, atrial fibrillation and Parkinson's disease, compared to normal individuals. It was also confirmed that, when isolating vesicles from *Faecalibacterium prausnitzii*, and treating macrophages therewith, the secretion of IL-6 and TNF-α by pathogenic vesicles was significantly inhibited, thus completing the present invention based on these findings.

Thus, an object of the present invention is to provide a method of providing information for diagnosis of gastric cancer, colorectal cancer, liver cancer, pancreatic cancer, cholangiocarcinoma, ovarian cancer, bladder cancer, lymphoma, myocardial infarction, atrial fibrillation or Parkinson's disease.

Further, another object of the present invention is to provide a composition for preventing, alleviating or treating one or more diseases selected from the group consisting of gastric cancer, colorectal cancer, liver cancer, pancreatic cancer, cholangiocarcinoma, ovarian cancer, bladder cancer, lymphoma, myocardial infarction, atrial fibrillation and Parkinson's disease, comprising *Faecalibacterium prausnitzii*-derived vesicles as an active ingredient.

However, a technical problem to be achieved by the present invention is not limited to the aforementioned problems, and the other problems that are not mentioned may be clearly understood by a person skilled in the art from the following description.

Technical Solution

To achieve the object of the present invention as described above, the present invention provides a method of providing information for diagnosing gastric cancer, colorectal cancer, liver cancer, pancreatic cancer, cholangiocarcinoma, ovarian cancer, bladder cancer, lymphoma, myocardial infarction, atrial fibrillation, or Parkinson's disease, the method comprising the following steps:

(a) extracting DNAs from vesicles isolated from samples of a normal individual and a subject;

(b) performing polymerase chain reaction (PCR) on the extracted DNA using a pair of primers prepared based on a gene sequence present in 16S rDNA to obtain each PCR product; and (c) determining a case in which a content of vesicles derived from *Faecalibacterium prausnitzii* is lower than that of the normal individual sample, as gastric cancer, colorectal cancer, liver cancer, pancreatic cancer, cholangiocarcinoma, ovarian cancer, bladder cancer, lymphoma, myocardial infarction, atrial fibrillation, or Parkinson's disease, through quantitative analysis of the PCR product.

In addition, the present invention provides a method of diagnosing gastric cancer, colorectal cancer, liver cancer, pancreatic cancer, cholangiocarcinoma, ovarian cancer, bladder cancer, lymphoma, myocardial infarction, atrial fibrillation, or Parkinson's disease, the method comprising the following steps:

(a) extracting DNAs from vesicles isolated from samples of a normal individual and a subject;

(b) performing polymerase chain reaction (PCR) on the extracted DNA using a pair of primers prepared based on a gene sequence present in 16S rDNA to obtain each PCR product; and (c) determining a case in which a content of vesicles derived from *Faecalibacterium prausnitzii* is lower than that of the normal individual sample, as gastric cancer, colorectal cancer, liver cancer, pancreatic cancer, cholangiocarcinoma, ovarian cancer, bladder cancer, lymphoma, myocardial infarction, atrial fibrillation, or Parkinson's disease, through quantitative analysis of the PCR product.

As an exemplary embodiment of the present invention, the sample in Step (a) may be stool, blood, or urine.

As another embodiment of the present invention, the primer pair in Step (b) may be a primer pair comprising base sequences represented by SEQ ID Nos. 1 and 2.

Further, the present invention provides a pharmaceutical composition for preventing or treating one or more diseases selected from the group consisting of gastric cancer, colorectal cancer, liver cancer, pancreatic cancer, cholangiocarcinoma, ovarian cancer, bladder cancer, lymphoma, myocardial infarction, atrial fibrillation, and Parkinson's disease, comprising vesicles derived from *Faecalibacterium prausnitzii* as an active ingredient.

Further, the present invention provides a food composition for preventing or alleviating one or more diseases selected from the group consisting of gastric cancer, colorectal cancer, liver cancer, pancreatic cancer, cholangiocarcinoma, ovarian cancer, bladder cancer, lymphoma, myocardial infarction, atrial fibrillation, and Parkinson's disease, comprising vesicles derived from *Faecalibacterium prausnitzii* as an active ingredient.

Furthermore, the present invention provides a method of preventing or treating one or more diseases selected from the group consisting of gastric cancer, colorectal cancer, liver cancer, pancreatic cancer, cholangiocarcinoma, ovarian cancer, bladder cancer, lymphoma, myocardial infarction, atrial fibrillation, and Parkinson's disease, the method comprising a step of administering a pharmaceutical composition comprising vesicles derived from *Faecalibacterium prausnitzii* as an active ingredient to a subject.

Further, the present invention provides a use of vesicles derived from *Faecalibacterium prausnitzii* for preventing or treating one or more diseases selected from the group consisting of gastric cancer, colorectal cancer, liver cancer, pancreatic cancer, cholangiocarcinoma, ovarian cancer, bladder cancer, lymphoma, myocardial infarction, atrial fibrillation, and Parkinson's disease.

As an exemplary embodiment of the present invention, the vesicles may have an average diameter of 10 to 200 nm.

As another exemplary embodiment of the present invention, the vesicles may be secreted naturally or artificially from *Faecalibacterium prausnitzii*.

Advantageous Effects

The present inventors confirmed that intestinal bacteria are not absorbed into the body, but vesicles derived from bacteria are absorbed into the body through epithelial cells, systemically distributed, and excreted from the body through the kidneys, liver, and lungs, and that through a metagenomic analysis of vesicles derived from bacteria present in the stool, blood, or urine of a patient, vesicles derived from *Faecalibacterium prausnitzii* present in the stool, blood, or urine of patients with gastric cancer, colorectal cancer, liver cancer, pancreatic cancer, cholangiocarcinoma, ovarian cancer, bladder cancer, lymphoma, myocardial infarction, atrial fibrillation, and Parkinson's disease had been significantly decreased as compared to those in normal individual. In addition, it has been observed that when intestinal symbiotic *Faecalibacterium prausnitzii* is isolated, cultured in vitro to isolate vesicles, and the vesicles are administered into inflammatory cells in vitro, the secretion of inflammatory mediators caused by pathogenic vesicles are significantly inhibited. Therefore, the *Faecalibacterium prausnitzii*-derived vesicles according to the present invention are expected to be effectively used for a method of diagnosing diseases, such as gastric cancer, colorectal cancer, liver cancer, pancreatic cancer, cholangiocarcinoma, ovarian cancer, bladder cancer, lymphoma, myocardial infarction, atrial fibrillation and Parkinson's disease, and a food or drug composition for preventing, alleviating or treating the above-mentioned diseases.

DESCRIPTION OF DRAWINGS

FIGS. 13A and 13B show results of comparing the secretion of inflammatory mediators by treating macrophages with various concentrations of *Faecalibacterium prausnitzii*-derived vesicles with that by treating macrophages with pathogenic vesicles such as *Escherichia coli* vesicles (*E. coli* EVs) to evaluate an inflammation-inducing effect of *Faecalibacterium prausnitzii*-derived vesicles, wherein FIG. 13A is the comparison result of IL-6 secretion, and FIG. 13B is the comparison result of TNF-α secretion.

FIGS. 14A and 14B show results of evaluating an effect on the secretion of inflammatory mediators caused by *E. coli* EVs by pretreating *Faecalibacterium prausnitzii*-derived vesicles before treatment of pathogenic vesicles such as *E. coli* EVs to evaluate anti-inflammatory and immunomodulatory effects of *Faecalibacterium prausnitzii*-derived vesicles, wherein FIG. 14A is the comparison of IL-6 secretion, and FIG. 14B is the comparison of TNF-α secretion.

BEST MODES

Figure 1A:
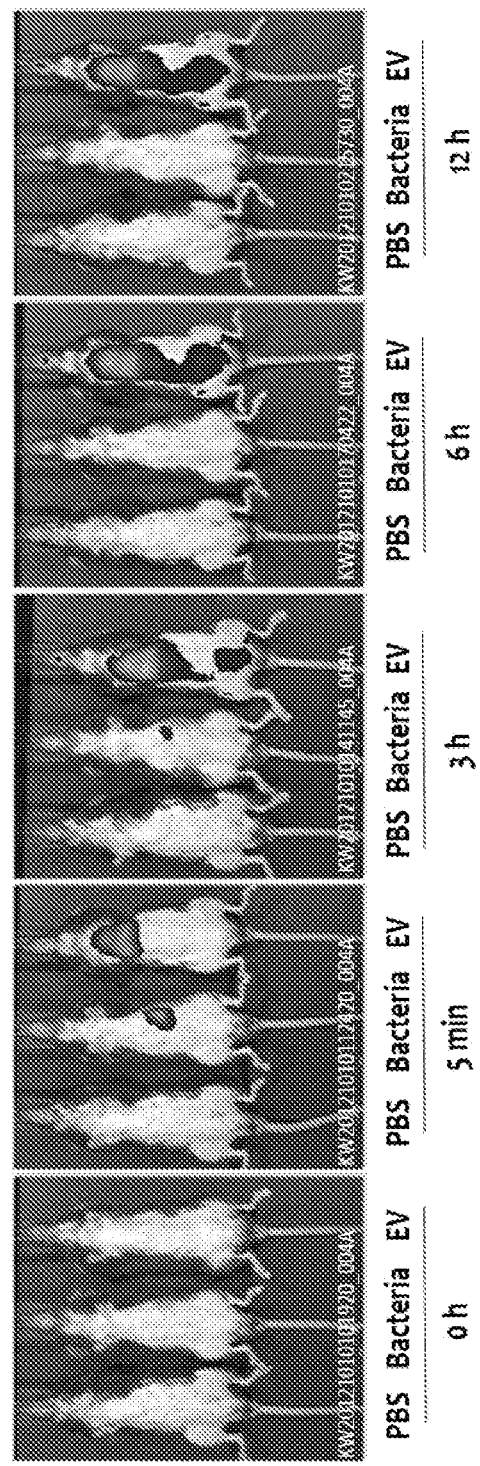
FIG. 1A is a series of photographs capturing distribution patterns of bacteria and bacteria-derived vesicles (EV) by time after the bacteria and the vesicles derived from bacteria were orally administered to mice.

The present invention relates to vesicles derived from *Faecalibacterium prausnitzii* and a use thereof.

The present inventors confirmed through metagenomic analysis that the content of vesicles derived from *Faecalibacterium prausnitzii* was remarkably reduced in samples derived from patients with gastric cancer, colorectal cancer, liver cancer, pancreatic cancer, cholangiocarcinoma, ovarian cancer, bladder cancer, lymphoma, myocardial infarction, atrial fibrillation, and Parkinson's disease as compared to that of the samples derived from normal individuals, thereby completing the present invention based on this.

Thus, the present invention provides a method of providing information for diagnosing gastric cancer, colorectal cancer, liver cancer, pancreatic cancer, cholangiocarcinoma, ovarian cancer, bladder cancer, lymphoma, myocardial infarction, atrial fibrillation, or Parkinson's disease, the method comprising the following steps:

(a) extracting DNAs from vesicles isolated from samples of a normal individual and a subject;

(b) performing polymerase chain reaction (PCR) on the extracted DNA using a pair of primers prepared based on a gene sequence present in 16S rDNA to obtain each PCR product; and (c) determining a case in which a content of vesicles derived from *Faecalibacterium prausnitzii* is lower than that of the normal individual sample, as gastric cancer, colorectal cancer, liver cancer, pancreatic cancer, cholangiocarcinoma, ovarian cancer, bladder cancer, lymphoma, myocardial infarction, atrial fibrillation, or Parkinson's disease, through quantitative analysis of the PCR product.

The term "diagnosis" as used herein refers to determination of a condition of a disease of a patient over all aspects, in a broad sense. The contents of the determination are the disease entity, the etiology, the pathogenesis, the severity, the detailed aspects of a disease, the presence and absence of complications, the prognosis, and the like. The diagnosis in the present invention means determining whether gastric cancer, colorectal cancer, liver cancer, pancreatic cancer, cholangiocarcinoma, ovarian cancer, bladder cancer, lymphoma, myocardial infarction, atrial fibrillation, and/or Parkinson's disease occur, the level of the disease, and the like.

The term "nanovesicle" or "vesicle" as used herein refers to a structure consisting of a nano-sized membrane secreted from various bacteria. Vesicles derived from gram-negative bacteria or outer membrane vesicles (OMVs) have endotoxins (lipopolysaccharides), toxic protein, bacterial DNA and RNA, and vesicles derived from gram-positive bacteria also have peptidoglycan and lipoteichoic acid which are cell wall components of bacteria in addition to proteins and nucleic acids. In the present invention, nanovesicles or vesicles are secreted naturally from *Faecalibacterium prausnitzii* or produced artificially, are in the form of a sphere, and have an average diameter of 10 to 200 nm.

The term "metagenome" as used herein also refers to a microbiome, and refers to a total of genomes including all viruses, bacteria, fungi, and the like in an isolated region such as soil and an animal's intestines, and is typically used as a concept of genomes explaining identification of a large number of microorganisms at one time by using a sequence analyzer in order to analyze uncultivated microorganisms. In particular, the metagenome does not refer to a genome of one species, but refers to a kind of mixed genome as a genome of all species of one environmental unit. The metagenome is, when one species is defined in the development process of omics biology, a term derived from the viewpoint of making a complete species is made by various species interacting with each other as well as one kind of functionally existing species. Technically, the metagenome is an object of a technique to identify all species in one environment and investigate interactions and metabolism by analyzing all DNAs and RNAs regardless of species using a rapid sequence analysis method.

In the present invention, the sample derived from patients may be stool, blood, or urine, but is not limited thereto.

As another aspect of the present invention, the present invention provides a pharmaceutical composition for preventing or treating one or more diseases selected from the group consisting of gastric cancer, colorectal cancer, liver cancer, pancreatic cancer, cholangiocarcinoma, ovarian cancer, bladder cancer, lymphoma, myocardial infarction, atrial fibrillation, and Parkinson's disease, comprising vesicles derived from *Faecalibacterium prausnitzii* as an active ingredient.

As another aspect of the present invention, the present invention provides a food composition for preventing or alleviating one or more diseases selected from the group consisting of gastric cancer, colorectal cancer, liver cancer, pancreatic cancer, cholangiocarcinoma, ovarian cancer, bladder cancer, lymphoma, myocardial infarction, atrial fibrillation, and Parkinson's disease, comprising vesicles derived from *Faecalibacterium prausnitzii* as an active ingredient.

The term "prevention" as used herein refers to all actions that suppress gastric cancer, colorectal cancer, liver cancer, pancreatic cancer, cholangiocarcinoma, ovarian cancer, bladder cancer, lymphoma, myocardial infarction, atrial fibrillation, and/or Parkinson's disease, and the like or delay the onset thereof via administration of the food or pharmaceutical composition according to the present invention.

The term "treatment" as used herein refers to all actions that alleviate or beneficially change symptoms of gastric cancer, colorectal cancer, liver cancer, pancreatic cancer, cholangiocarcinoma, ovarian cancer, bladder cancer, lymphoma, myocardial infarction, atrial fibrillation, and/or Parkinson's disease and the like via administration of the food or pharmaceutical composition according to the present invention.

The term "alleviation" used as used herein refers to all actions that at least reduce a parameter associated with a condition to be treated, for example, the degree of symptoms.

The vesicles may be isolated from a culturing solution comprising *Faecalibacterium prausnitzii* by using one or more methods selected from the group consisting of centrifugation, ultra-high speed centrifugation, high pressure treatment, extrusion, sonication, cell lysis, homogenization, freezing-thawing, electroporation, mechanical decomposition, chemical treatment, filtration by a filter, gel filtration chromatography, free-flow electrophoresis, and capillary electrophoresis. Further, a process such as washing for removing impurities and concentration of obtained vesicles may be further included.

In one embodiment of the present invention, as a result of orally administering bacteria and bacteria-derived vesicles to mice and observing in vivo absorption, distribution, and excretion patterns of the bacteria and the vesicles, it was confirmed that, while the bacteria were not absorbed via the intestinal mucous membrane, the bacteria-derived vesicles were absorbed within 5 minutes after administration and systemically distributed, and excreted via the kidneys, liver, and the like (see Example 1).

In one embodiment of the present invention, a bacterial metagenomic analysis was performed using vesicles isolated from the stool, blood, or urine of patients with gastric cancer, colorectal cancer, liver cancer, pancreatic cancer, cholangiocarcinoma, ovarian cancer, bladder cancer, lymphoma, myocardial infarction, atrial fibrillation, and Parkinson's disease and normal individuals who were matched in age and sex with the patients. As a result, it was confirmed that vesicles derived from *Faecalibacterium prausnitzii* were significantly decreased in clinical samples of patients with gastric cancer, colorectal cancer, liver cancer, pancreatic cancer, cholangiocarcinoma, ovarian cancer, bladder cancer, lymphoma, myocardial infarction, atrial fibrillation, and Parkinson's disease as compared to samples of normal individuals (see Examples 3 to 13).

In another embodiment of the present invention, *Faecalibacterium prausnitzii* was cultured to evaluate whether vesicles secreted therefrom have immunomodulatory and anti-inflammatory effects, and it was confirmed that IL-6 and TNF-α secretion caused by *Escherichia coli* vesicles (*E. coli* EVs) are effectively inhibited by *Faecalibacterium prausnitzii*-derived vesicles through evaluation of the secretion of inflammatory mediators by treating *E. coli* EVs, which are an inflammatory disease causative factor, following treatment of macrophages with various concentrations of *Faecalibacterium prausnitzii*-derived vesicles (refer to Example 15).

The pharmaceutical composition of the present invention may include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Further, the composition may be formulated into an injectable formulation, such as an aqueous solution, a suspension, and an emulsion, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the method disclosed in the Remington's literature. The pharmaceutical composition of the present invention is not particularly limited in formulation, but may be formulated into an injection, an inhalant, an external preparation for skin, an oral ingestion, or the like.

The pharmaceutical composition of the present invention may be administered orally or parenterally (e.g., intravenously, subcutaneously, intradermally, intranasally or intratracheally) according to a desired method, and a dose may vary according to the condition and body weight of a patient, the severity of a disease, a drug formulation, an administration route, and duration, but may be suitably selected by those of ordinary skill in the art.

The pharmaceutical composition according to the present invention is administered in a pharmaceutically effective amount. In the present invention, the pharmaceutically effective amount refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields. The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

Specifically, an effective amount of the pharmaceutical composition according to the present invention may vary according to a patient's age, gender and body weight, and generally, the pharmaceutical composition may be administered at 0.001 to 150 mg, and preferably, 0.01 to 100 mg per kg of body weight daily or every two days, or 1 to 3 times daily. However, as the dose may be increased or decreased by an administration route, the severity of obesity, gender, a body weight or an age, the above-mentioned dose does not limit the scope of the present invention in any way.

The food composition of the present invention includes a health functional food composition. The food composition according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials. However, for long-term intake for the purpose of health and hygiene or for the purpose of health control, the amount may be less than the above-mentioned range.

Other ingredients are not particularly limited, except that the food composition of the present invention contains the active ingredient as an essential ingredient at the indicated ratio, and the food composition of the present invention may contain various flavorants, natural carbohydrates, and the like, like a typical beverage, as an additional ingredient. Examples of the above-described natural carbohydrate include common sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavorant other than those described above, a natural flavorant (thaumatin, stevia extract (for example, rebaudioside A, glycyrrhizin and the like), and a synthetic flavorant (saccharin, aspartame and the like) may be advantageously used. The proportion of the natural carbohydrate may be appropriately determined by the choice of those of ordinary skill in the art.

The food composition of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, in addition to the additives. These ingredients may be used either alone or in combinations thereof. The ratio of these additives may also be appropriately selected by those of ordinary skill in the art.

Hereinafter, preferred Examples for helping the understanding of the present invention will be suggested. However, the following Examples are provided only to more easily understand the present invention, and the contents of the present invention are not limited by the following Examples.

MODES OF THE INVENTION

Examples

Example 1. Analysis of In Vivo Absorption, Distribution, and Excretion Patterns of Intestinal Bacteria and Vesicles Derived from Bacteria In order to evaluate whether intestinal bacteria and bacteria-derived vesicles were systemically absorbed through the gastrointestinal tract, an experiment was performed with the following method. First, a dose of 50 μg of each of fluorescence-labeled intestinal bacteria and intestinal bacteria-derived vesicles was administered through the gastrointestinal tract to the stomach of a mouse, and fluorescence was measured after 0 minute, 5 minutes, 3 hours, 6 hours, and 12 hours. As a result of observing the entire image of the mouse, as illustrated in FIG. 1A, the bacteria were not systemically absorbed, but the vesicles derived from bacteria were systemically absorbed 5 minutes after administration, and fluorescence was strongly observed in the bladder 3 hours after administration, so that it could be seen that the vesicles were excreted to the urinary tract. Further, it could be seen that the vesicles were present in the body until 12 hours after administration (see FIG. 1A).

Figure 1B:
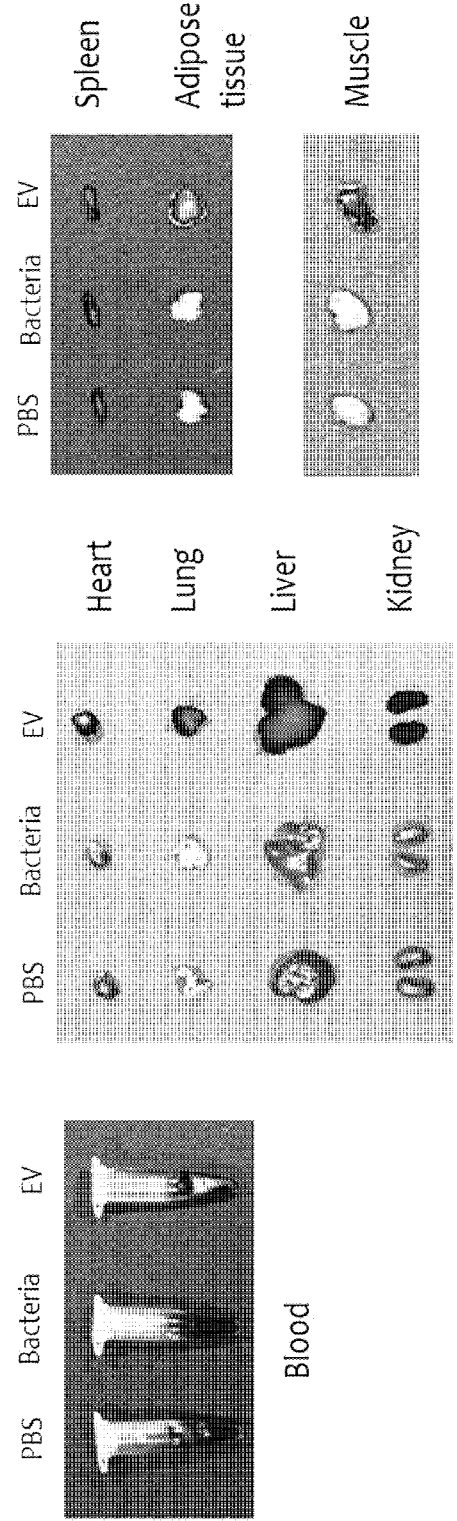
FIG. 1B is a result of evaluating the in vivo distribution patterns of the bacteria and the vesicles by harvesting blood, kidneys, liver, and various organs at 12 hours after orally administering the bacteria and the vesicles.

In order to evaluate the pattern in which the intestinal bacteria and the vesicles derived from the intestinal bacteria infiltrated into various organs after they were systemically absorbed, 50 μg of bacteria and vesicles derived from bacteria labeled with fluorescence were administered in the same manner as described above, and then the stool, blood, heart, lungs, liver, kidneys, spleen, fat, and muscle were collected 12 hours after administration. As a result of observing fluorescence in the collected tissues, as illustrated in FIG. 1B, it could be seen that the vesicles derived from bacteria were distributed in the stool, blood, heart, lungs, liver, spleen, fat, muscle, and kidneys but the bacteria were not absorbed (see FIG. 1B).

Example 2. Metagenomic Analysis of Vesicles Derived from Bacteria in Clinical Sample After clinical samples such as stool, blood, urine, and the like was first put into a 10-ml tube and suspended matter was allowed to settle by a centrifuge (3,500×g, 10 min, 4° C.), only the supernatant was transferred to a new 10-ml tube. After bacteria and impurities were removed by using a 0.22-μm filter, they were transferred to a Centriprep tube (centrifugal filters 50 kD) and centrifuged at 1,500×g and 4° C. for 15 minutes, materials smaller than 50 kD were discarded, and the residue was concentrated to 10 ml. After bacteria and impurities were removed once again by using a 0.22-μm filter, the supernatant was discarded by using a ultra-high speed centrifugation at 150,000×g and 4° C. for 3 hours with a Type 90Ti rotor, and an aggregated pellet was dissolved in physiological saline (PBS).

Internal DNA was extracted out of the lipid by boiling 100 μl of the vesicles isolated by the above method at 100° C., and then cooled on ice for 5 minutes. And then, in order to remove the remaining suspended matter, the DNA was centrifuged at 10,000×g and 4° C. for 30 minutes, and only the supernatant was collected. And, the amount of DNA was quantified by using Nanodrop. Thereafter, in order to confirm whether the DNA derived from bacteria was present in the extracted DNA, PCR was performed with 16s rDNA primers shown in the following Table 1 and it was confirmed that genes derived from bacteria were present in the extracted genes.

performed (Illumina MiSeq sequencer), the results were output as a standard flowgram format (SFF) file, the SFF file was converted into a sequence file (.fasta) and a nucleotide quality score file using GS FLX software (v2.9), and then the reliability estimation for the reads was confirmed, and a portion in which the window (20 bps) average base call accuracy was less than 99% (Phred score<20) was removed. For the OTU (operational taxonomy unit) analysis, clustering was performed according to sequence similarity by using UCLUST and USEARCH, the genus, family, order, class, and phylum were clustered based on 94%, 90%, 85%, 80%, and 75% sequence similarity, respectively, classification was performed at the phylum, class, order, family, and genus levels of each OUT, and bacteria having a sequence similarity of 97% or more at the genus level were profiled by using the 16S RNA sequence database (108,453 sequences) of BLASTN and GreenGenes (QIIME).

Figure 2:
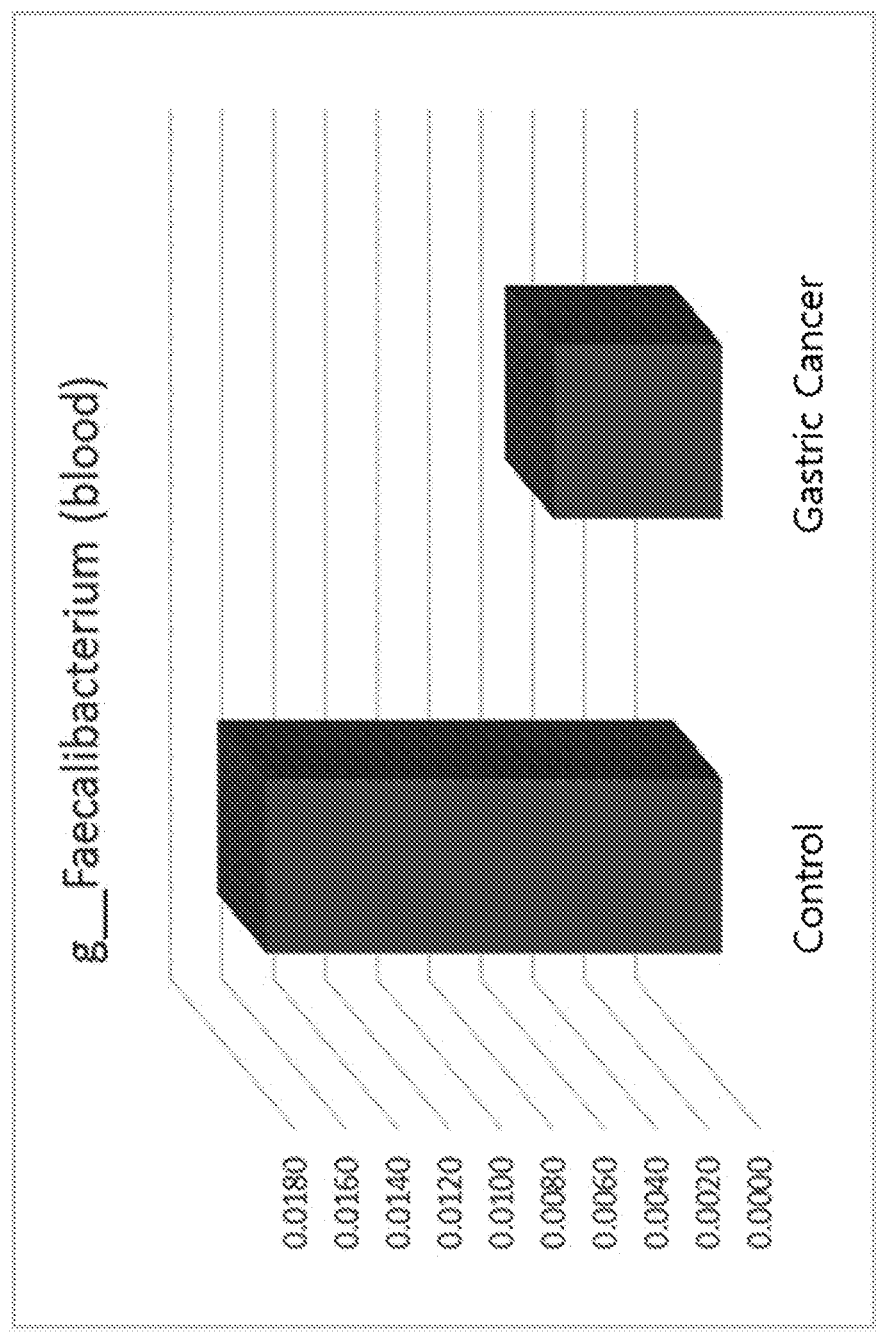
FIG. 2 is a result of comparing the distributions of vesicles derived from *Faecalibacterium prausnitzii* after metagenomic analysis of bacteria-derived vesicles present in the blood of gastric cancer patients and a normal individuals.

Example 3. Metagenomic Analysis of Bacteria-Derived Vesicles in Blood of Patient with Gastric Cancer After a metagenomic analysis was performed using the method of Example 2 on the blood from 66 patients with gastric cancer, and 198 normal individuals who were matched in age and sex by extracting genes from vesicles present in the blood, the distribution of vesicles derived from *Faecalibacterium prausnitzii* was evaluated. As a result, it was confirmed that vesicles derived from *Faecalibacterium prausnitzii* were significantly decreased in the blood from the patients with gastric cancer as compared to the blood from the normal individuals (see Table 2 and FIG. 2).

TABLE 2

| | Blood | | | | | |
|---|---|---|---|---|---|---|
| | Control | | Gastric Cancer | | t-test | |
| Taxon | Mean | SD | Mean | SD | p-value | Ratio |
| g__Faecalibacterium | 0.0176 | 0.0243 | 0.0065 | 0.0090 | <0.0001 | 0.37 |

TABLE 1

| primer | | Sequence | SEQ ID No. |
|---|---|---|---|
| 16S rDNA | 16S_V3_F | 5'-TCGTCGGCAGCGTCAGATG TGTATAAGAGACAGCCTACGGG NGGCWGCAG-3' | 1 |
| | 16S_V4_R | 5'-GTCTCGTGGGCTCGGAGAT GTGTATAAGAGACAGGACTACH VGGGTATCTAATCC | 2 |

The DNA extracted by the above method was amplified using the 16S rDNA primers, and then sequencing was

Figure 3:
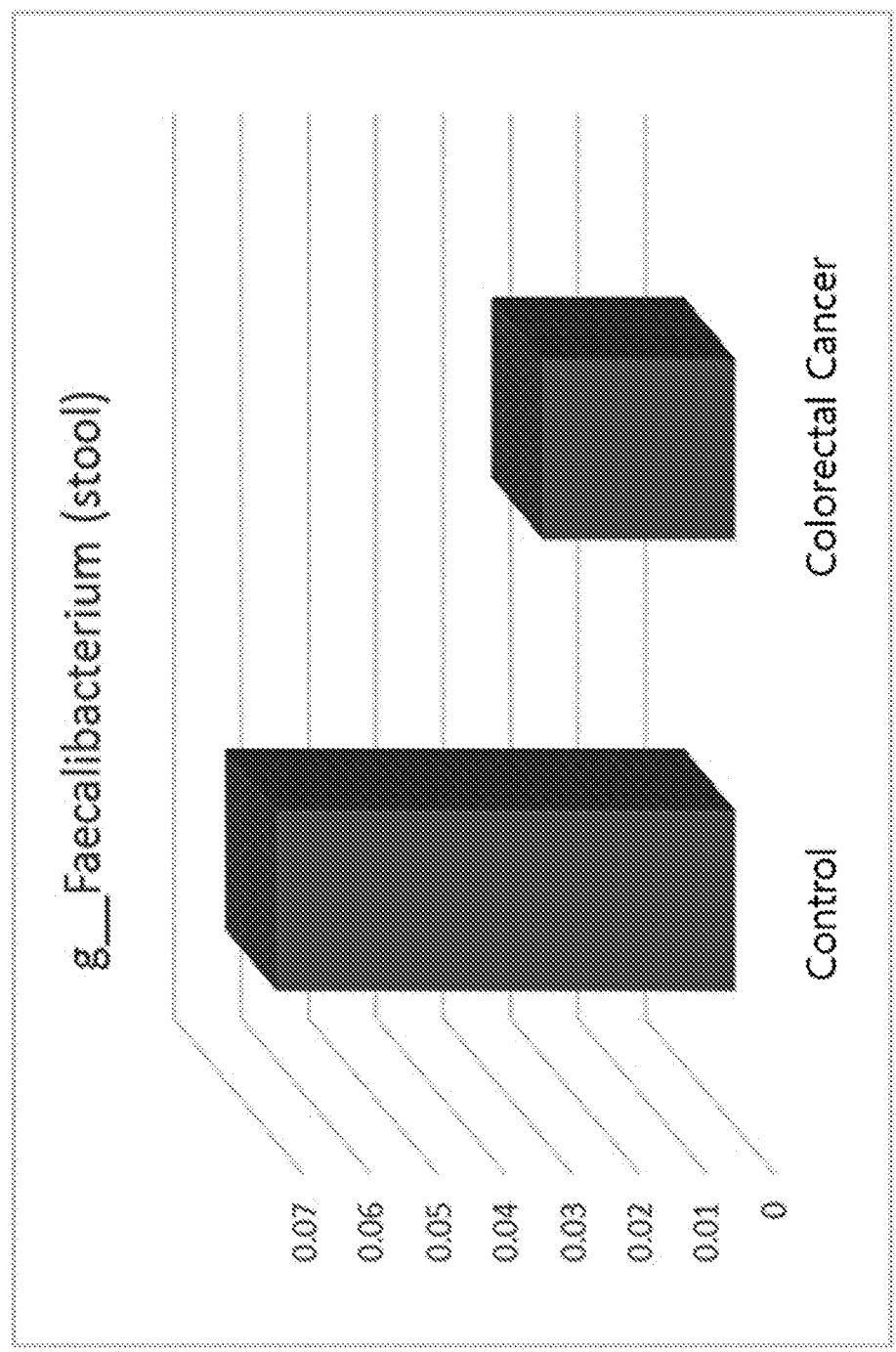
FIG. 3 is a result of comparing the distributions of vesicles derived from *Faecalibacterium prausnitzii* after metagenomic analysis of bacteria-derived vesicles present in the stool of colorectal cancer patients and a normal individuals.

Example 4. Metagenomic Analysis of Bacteria-Derived Vesicles in Stool of Patient with Colorectal Cancer After a metagenomic analysis was performed using the method of Example 2 on the stool from 29 patients with colorectal cancer, and 358 normal individuals who were matched in age and sex by extracting genes from vesicles present in the stool, the distribution of vesicles derived from *Faecalibacterium prausnitzii* was evaluated. As a result, it was confirmed that vesicles derived from *Faecalibacterium prausnitzii* were significantly decreased in the stool from the patients with colorectal cancer as compared to the stool from the normal individuals (see Table 3 and FIG. 3).

TABLE 3

| | Stool | | | | | |
|---|---|---|---|---|---|---|
| | Control | | Colorectal Cancer | | t-test | |
| Taxon | Mean | SD | Mean | SD | p-value | Ratio |
| g__Faecalibacterium | 0.0681 | 0.0882 | 0.0285 | 0.0584 | 0.002 | 0.42 |

Figure 4:
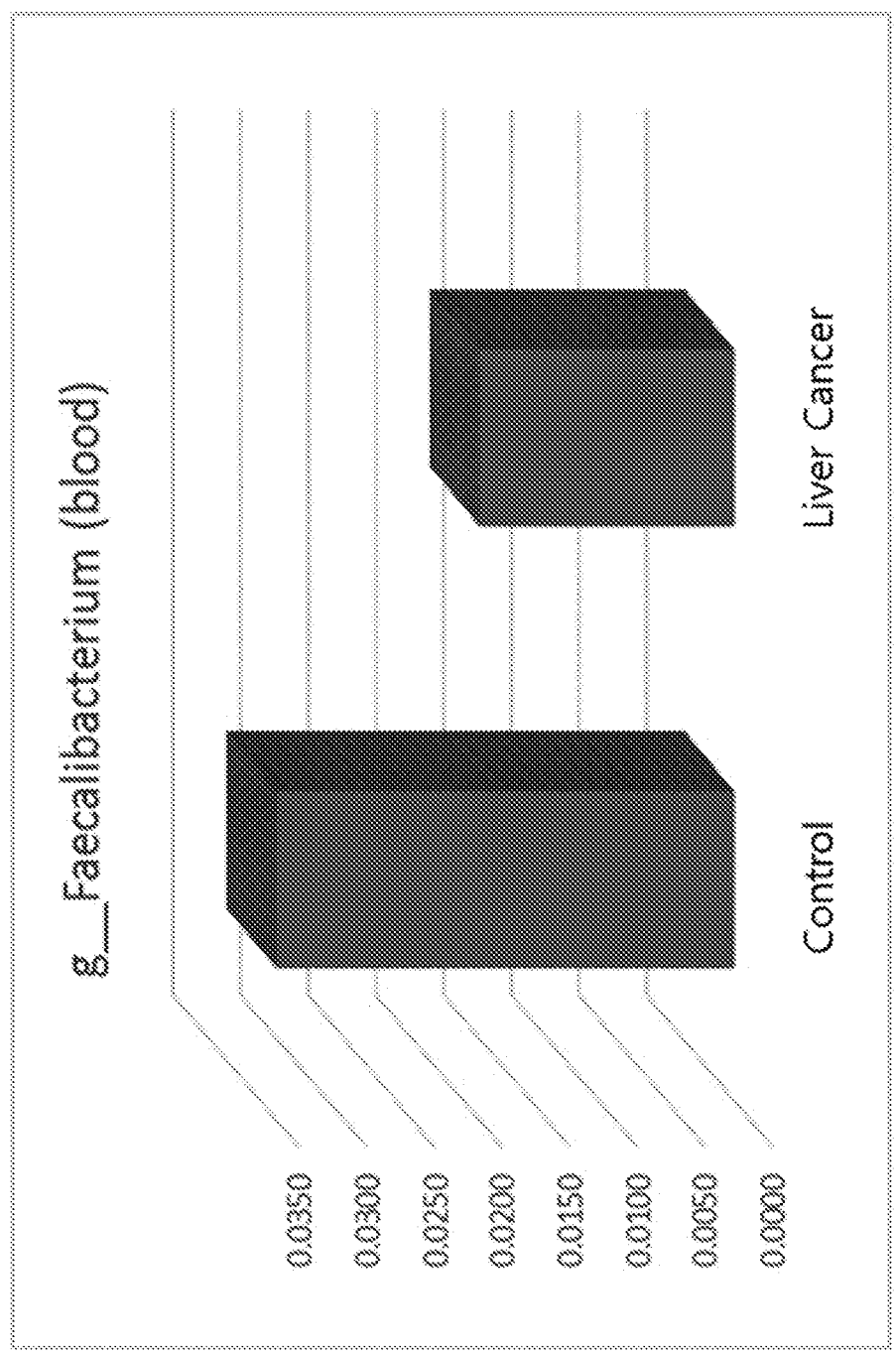
FIG. 4 is a result of comparing the distributions of vesicles derived from *Faecalibacterium prausnitzii* after metagenomic analysis of bacteria-derived vesicles present in the blood of liver cancer patients and a normal individuals.

Example 5. Metagenomic Analysis of Bacteria-Derived Vesicles in Blood of Patient with Liver Cancer After a metagenomic analysis was performed using the method of Example 2 on the blood from 86 patients with liver cancer, and 331 normal individuals who were matched in age and sex by extracting genes from vesicles present in the blood, the distribution of vesicles derived from *Faecalibacterium prausnitzii* was evaluated. As a result, it was confirmed that vesicles derived from *Faecalibacterium prausnitzii* were significantly decreased in the blood from the patients with liver cancer as compared to the blood from the normal individuals (see Table 4 and FIG. 4).

TABLE 4

| | Blood | | | | | |
| --- | --- | --- | --- | --- | --- | --- |
| | Control | | Liver Cancer | | t-test | |
| Taxon | Mean | SD | Mean | SD | p-value | Ratio |
| g_Faecalibacterium | 0.0338 | 0.0268 | 0.0188 | 0.0188 | <0.0001 | 0.56 |

Figure 5:
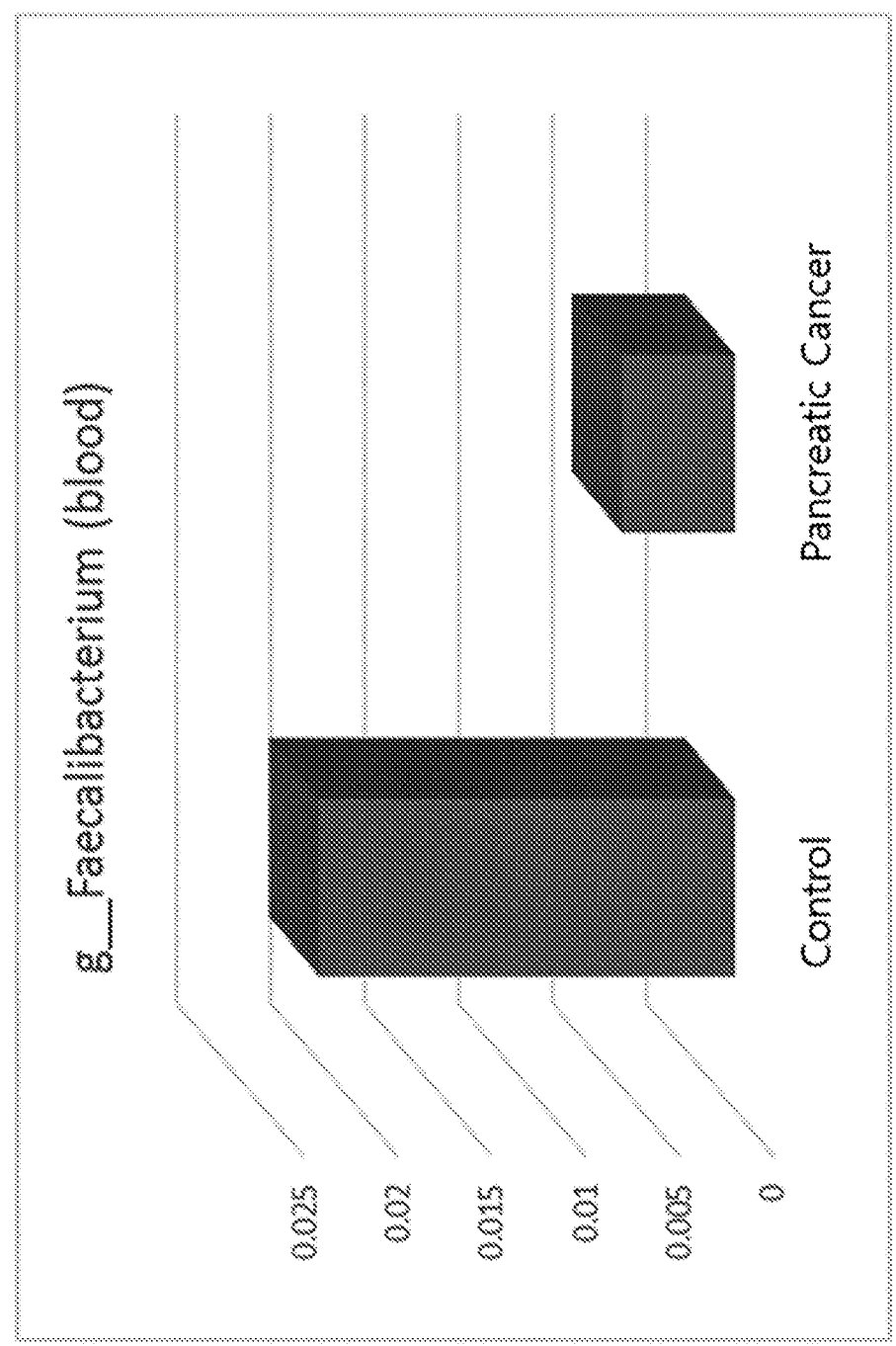
FIG. 5 is a result of comparing the distributions of vesicles derived from *Faecalibacterium prausnitzii* after metagenomic analysis of bacteria-derived vesicles present in the blood of pancreatic cancer patients and a normal individuals.

Example 6. Metagenomic Analysis of Bacteria-Derived Vesicles in Blood of Patient with Pancreatic Cancer After a metagenomic analysis was performed using the method of Example 2 on the blood from 176 patients with pancreatic cancer, and 271 normal individuals who were matched in age and sex by extracting genes from vesicles present in the blood, the distribution of vesicles derived from *Faecalibacterium prausnitzii* was evaluated. As a result, it was confirmed that vesicles derived from *Faecalibacterium prausnitzii* were significantly decreased in the blood from the patients with pancreatic cancer as compared to the blood from the normal individuals (see Table 5 and FIG. 5).

TABLE 5

| | Blood | | | | | |
| --- | --- | --- | --- | --- | --- | --- |
| | Control | | Pancreatic Cancer | | t-test | |
| Taxon | Mean | SD | Mean | SD | p-value | Ratio |
| g_Faecalibacterium | 0.0221 | 0.0282 | 0.006 | 0.0077 | <0.0001 | 0.27 |

Figure 6:
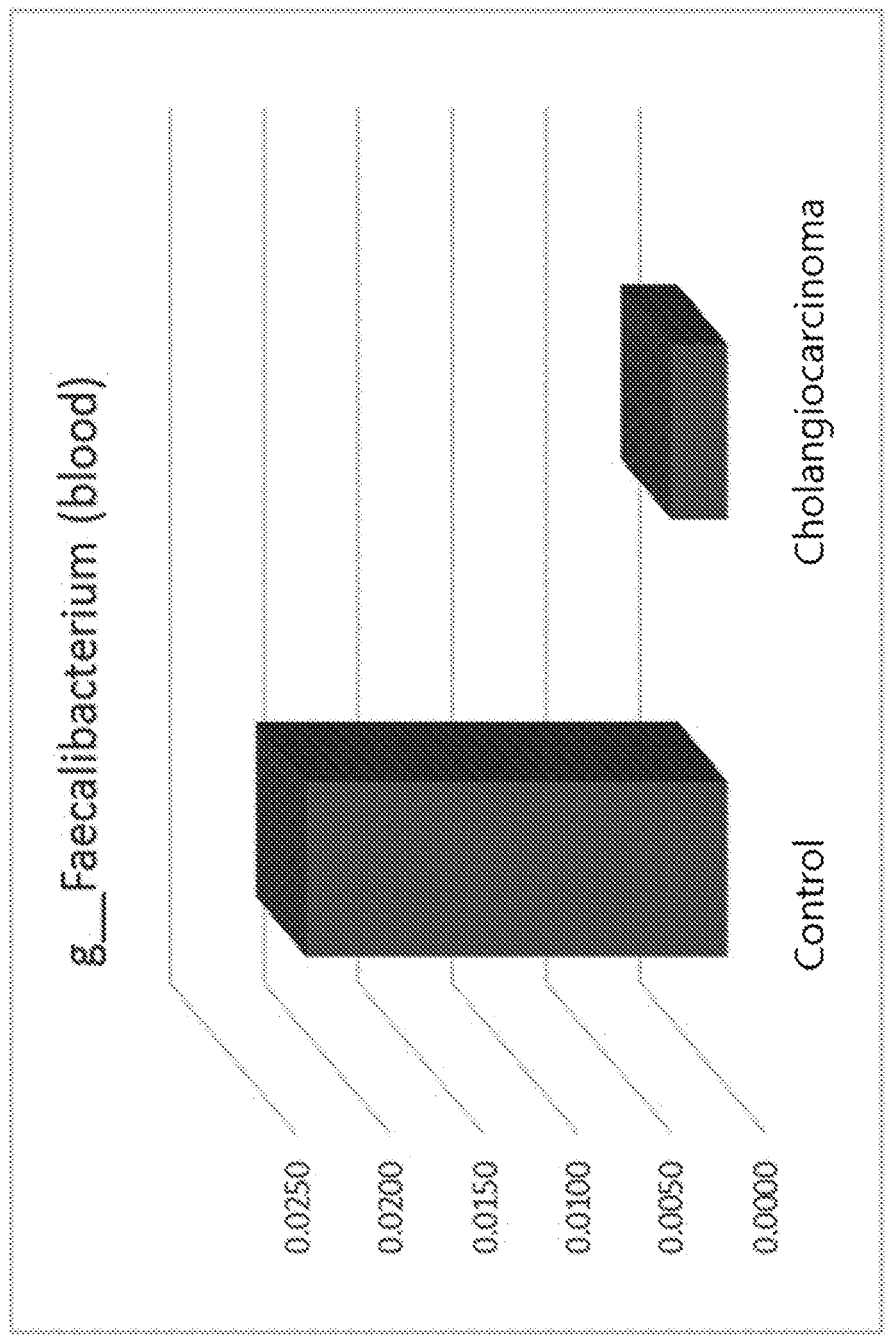
FIG. 6 is a result of comparing the distributions of vesicles derived from *Faecalibacterium prausnitzii* after metagenomic analysis of bacteria-derived vesicles present in the blood of cholangiocarcinoma patients and a normal individuals.

Example 7. Metagenomic Analysis of Bacteria-Derived Vesicles in Blood of Patient with Cholangiocarcinoma After a metagenomic analysis was performed using the method of Example 2 on the blood from 79 patients with cholangiocarcinoma, and 259 normal individuals who were matched in age and sex by extracting genes from vesicles present in the blood, the distribution of vesicles derived from *Faecalibacterium prausnitzii* was evaluated. As a result, it was confirmed that vesicles derived from *Faecalibacterium prausnitzii* were significantly decreased in the blood from the patients with cholangiocarcinoma as compared to the blood from the normal individuals (see Table 6 and FIG. 6).

TABLE 6

| | Blood | | | | | |
| --- | --- | --- | --- | --- | --- | --- |
| | Control | | Cholangiocarcinoma | | t-test | |
| Taxon | Mean | SD | Mean | SD | p-value | Ratio |
| g_Faecalibacterium | 0.0224 | 0.0288 | 0.0030 | 0.0059 | <0.0001 | 0.13 |

Figure 7:
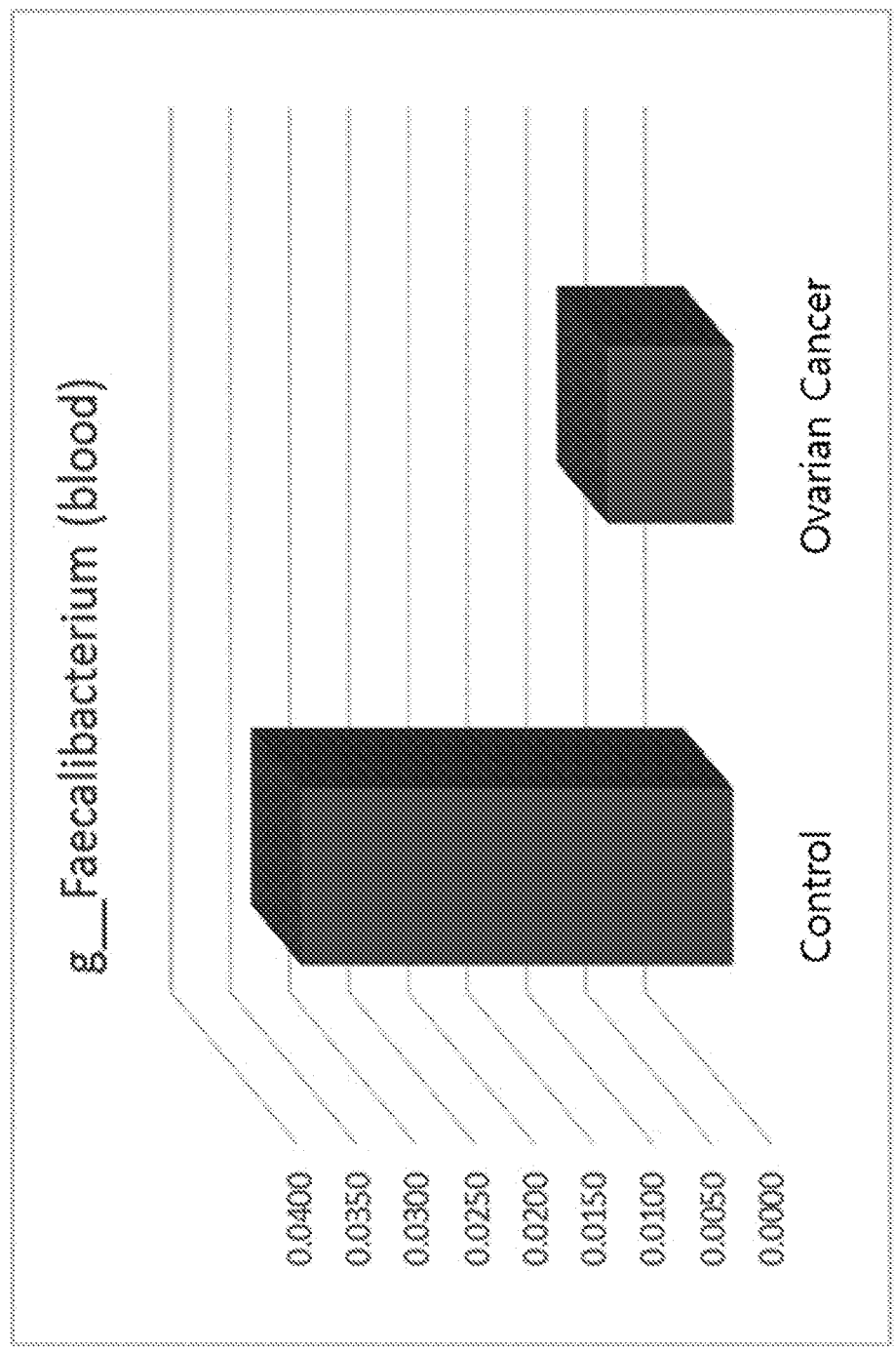
FIG. 7 is a result of comparing the distributions of vesicles derived from *Faecalibacterium prausnitzii* after metagenomic analysis of bacteria-derived vesicles present in the blood of ovarian cancer patients and a normal individuals.

Example 8. Metagenomic Analysis of Bacteria-Derived Vesicles in Blood of Patient with Ovarian Cancer After a metagenomic analysis was performed using the method of Example 2 on the blood from 137 patients with ovarian cancer, and 139 normal individuals who were matched in age and sex by extracting genes from vesicles present in the blood, the distribution of vesicles derived from *Faecalibacterium prausnitzii* was evaluated. As a result, it was confirmed that vesicles derived from *Faecalibacterium prausnitzii* were significantly decreased in the blood from the patients with ovarian cancer as compared to the blood from the normal individuals (see Table 7 and FIG. 7).

TABLE 7

| | Blood | | | | | |
| | Control | | Ovarian Cancer | | t-test | |
| Taxon | Mean | SD | Mean | SD | p-value | Ratio |
|---|---|---|---|---|---|---|
| g_Faecalibacterium | 0.0364 | 0.0389 | 0.0106 | 0.0088 | <0.0001 | 0.29 |

Figure 8:
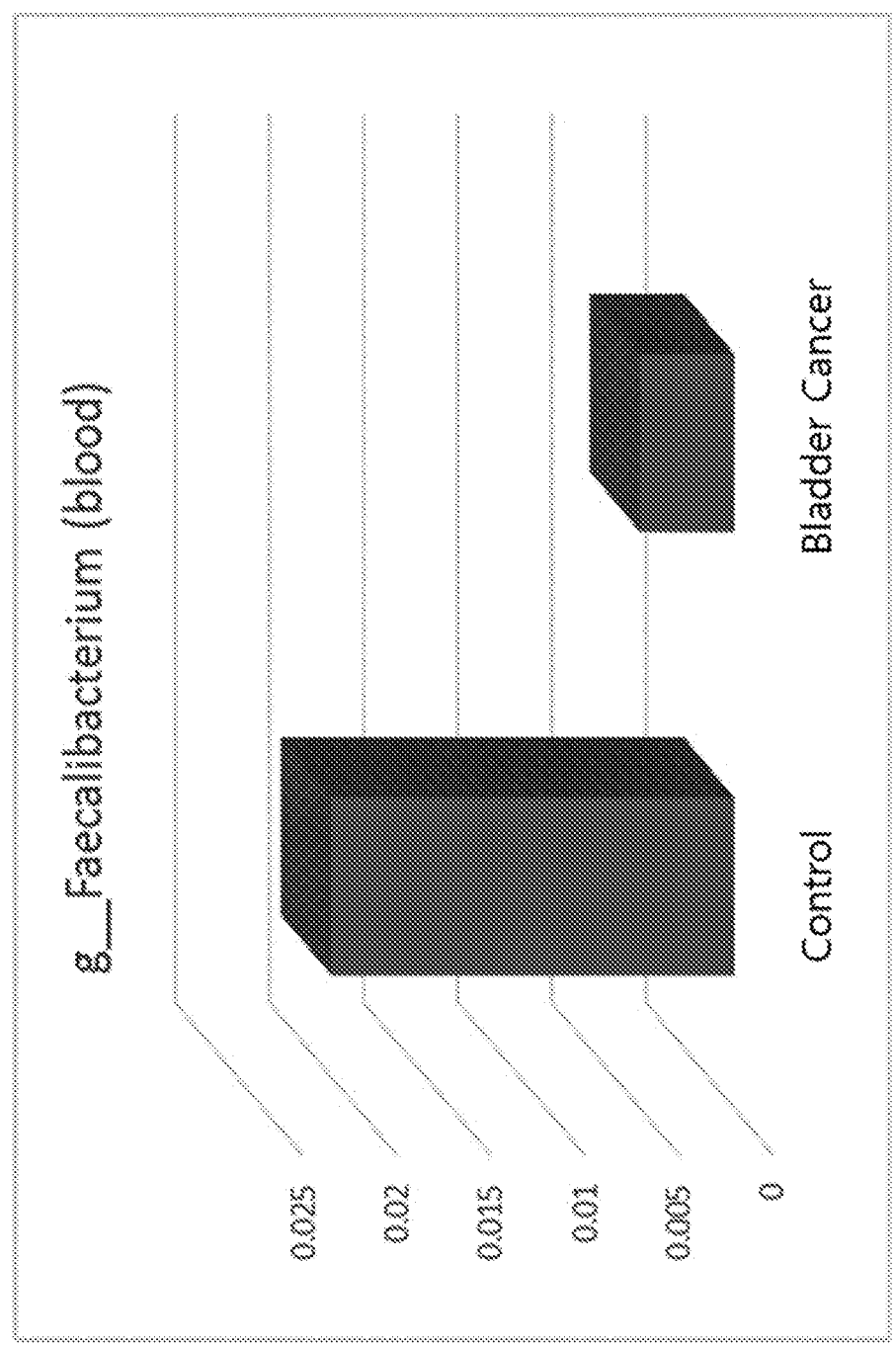
FIG. 8 is a result of comparing the distributions of vesicles derived from *Faecalibacterium prausnitzii* after metagenomic analysis of bacteria-derived vesicles present in the blood of bladder cancer patients and a normal individuals.

Example 9. Metagenomic Analysis of Bacteria-Derived Vesicles in Blood of Patient with Bladder Cancer After a metagenomic analysis was performed using the method of Example 2 on the blood from 91 patients with bladder cancer, and 176 normal individuals who were matched in age and sex by extracting genes from vesicles present in the blood, the distribution of vesicles derived from *Faecalibacterium prausnitzii* was evaluated. As a result, it was confirmed that vesicles derived from *Faecalibacterium prausnitzii* were significantly decreased in the blood from the patients with bladder cancer as compared to the blood from the normal individuals (see Table 8 and FIG. 8).

TABLE 8

| | Blood | | | | | |
| | Control | | Bladder Cancer | | t-test | |
| Taxon | Mean | SD | Mean | SD | p-value | Ratio |
|---|---|---|---|---|---|---|
| g_Faecalibacterium | 0.0214 | 0.0238 | 0.005 | 0.005 | <0.0001 | 0.23 |

Figure 9:
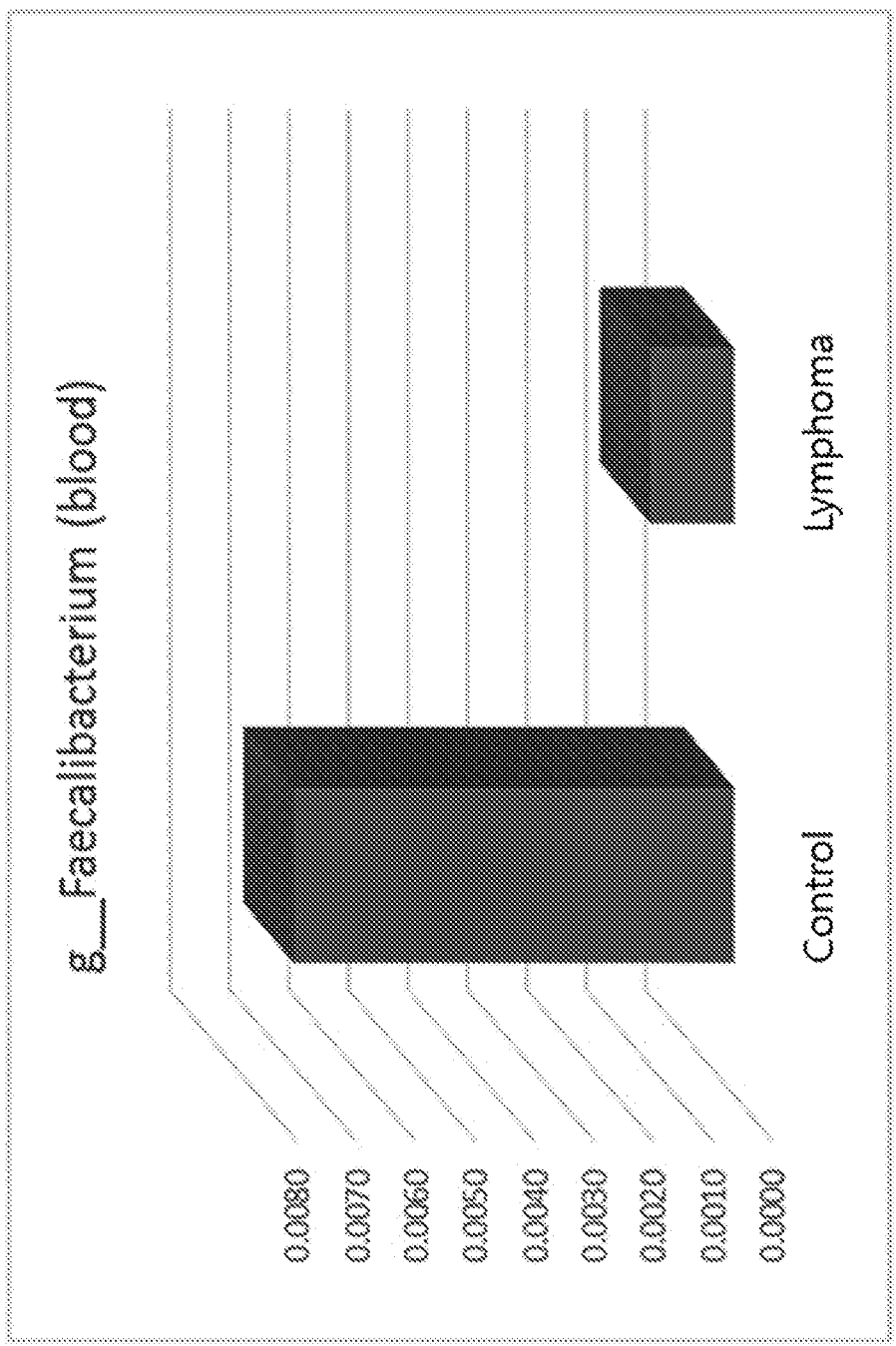
FIG. 9 is a result of comparing the distributions of vesicles derived from *Faecalibacterium prausnitzii* after metagenomic analysis of bacteria-derived vesicles present in the blood of lymphoma patients and a normal individuals.

Example 10. Metagenomic Analysis of Bacteria-Derived Vesicles in Blood of Patient with Lymphoma After a metagenomic analysis was performed using the method of Example 2 on the blood from 63 patients with lymphoma, and 53 normal individuals who were matched in age and sex by extracting genes from vesicles present in the blood, the distribution of vesicles derived from *Faecalibacterium prausnitzii* was evaluated. As a result, it was confirmed that vesicles derived from *Faecalibacterium prausnitzii* were significantly decreased in the blood from the patients with lymphoma as compared to the blood from the normal individuals (see Table 9 and FIG. 9).

TABLE 9

| | Blood | | | | | |
| | Control | | Lymphoma | | t-test | |
| Taxon | Mean | SD | Mean | SD | p-value | Ratio |
|---|---|---|---|---|---|---|
| g_Faecalibacterium | 0.0074 | 0.0100 | 0.0014 | 0.0025 | 0.0001 | 0.18 |

Figure 10:
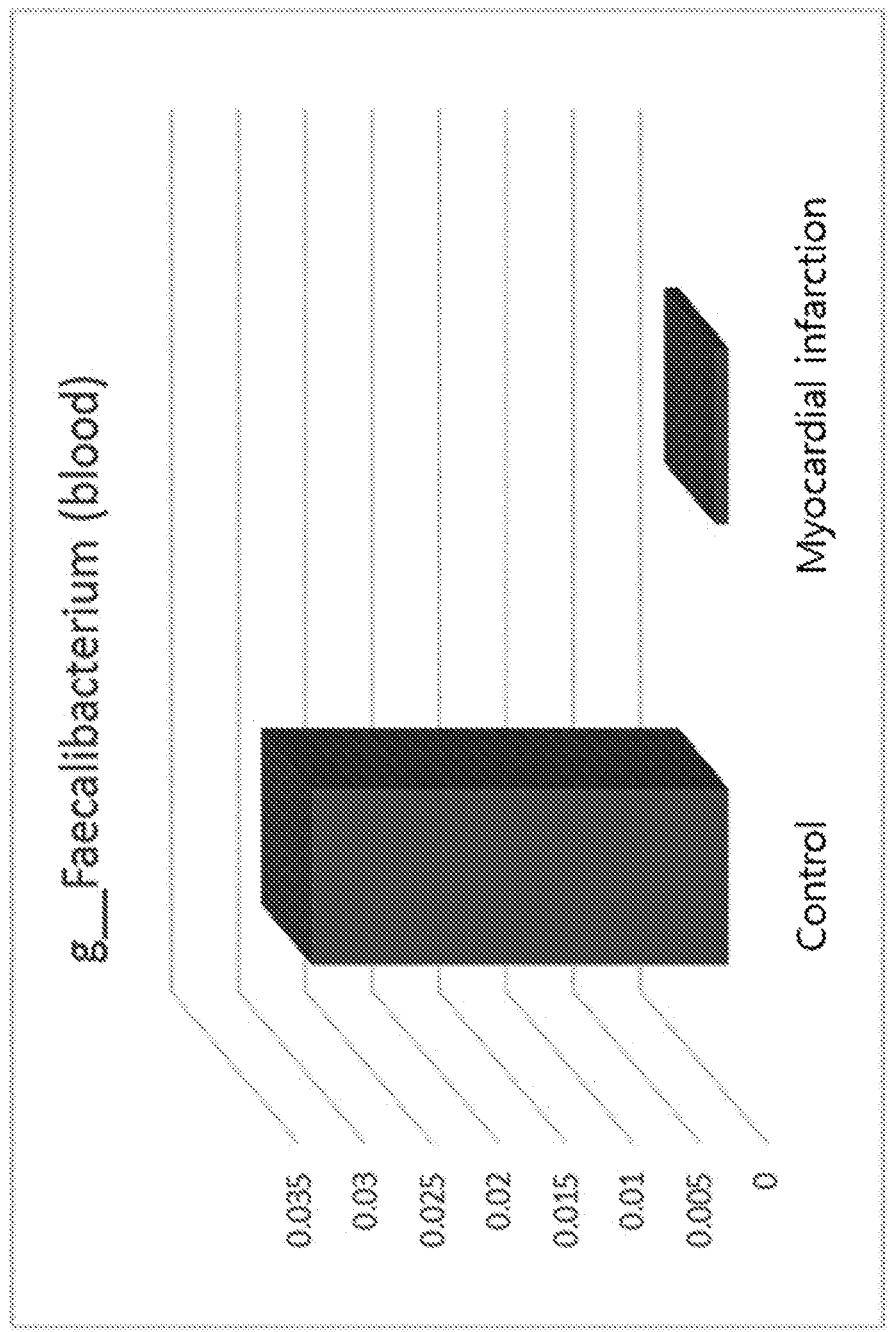
FIG. 10 is a result of comparing the distributions of vesicles derived from *Faecalibacterium prausnitzii* after metagenomic analysis of bacteria-derived vesicles present in the blood of myocardial infarction patients and a normal individuals.

Example 11. Metagenomic Analysis of Bacteria-Derived Vesicles in Blood of Patient with Myocardial Infarction After a metagenomic analysis was performed using the method of Example 2 on the blood from 57 patients with myocardial infarction, and 163 normal individuals who were matched in age and sex by extracting genes from vesicles present in the blood, the distribution of vesicles derived from *Faecalibacterium prausnitzii* was evaluated. As a result, it was confirmed that vesicles derived from *Faecalibacterium prausnitzii* were significantly decreased in the blood from the patients with myocardial infarction as compared to the blood from the normal individuals (see Table 10 and FIG. 10).

TABLE 10

| | Blood | | | | | |
|---|---|---|---|---|---|---|
| | Control | | Myocardial infarction | | t-test | |
| Taxon | Mean | SD | Mean | SD | p-value | Ratio |
| g_Faecalibacterium | 0.0311 | 0.031 | 0.001 | 0.0037 | <0.0001 | 0.03 |

Figure 11:
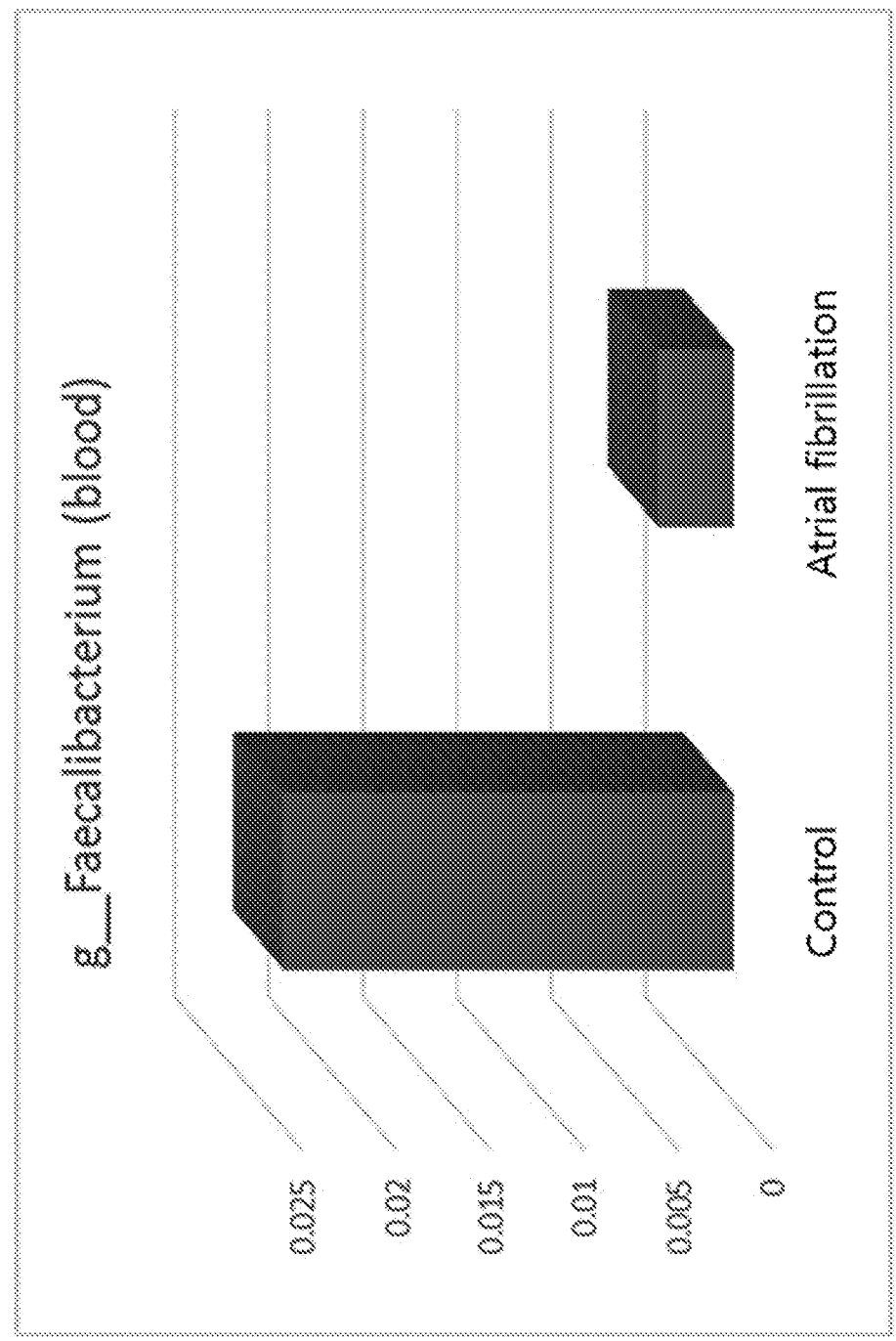
FIG. 11 is a result of comparing the distributions of vesicles derived from *Faecalibacterium prausnitzii* after metagenomic analysis of bacteria-derived vesicles present in the blood of atrial fibrillation patients and a normal individuals.

Example 12. Metagenomic Analysis of Bacteria-Derived Vesicles in Blood of Patient with Atrial Fibrillation After a metagenomic analysis was performed using the method of Example 2 on the blood from 34 patients with atrial fibrillation, and 62 normal individuals who were matched in age and sex by extracting genes from vesicles present in the blood, the distribution of vesicles derived from *Faecalibacterium prausnitzii* was evaluated. As a result, it was confirmed that vesicles derived from *Faecalibacterium prausnitzii* were significantly decreased in the blood from the patients with atrial fibrillation as compared to the blood from the normal individuals (see Table 11 and FIG. 11).

TABLE 11

| | Blood | | | | | |
|---|---|---|---|---|---|---|
| | Control | | Atrial fibrillation | | t-test | |
| Taxon | Mean | SD | Mean | SD | p-value | Ratio |
| g_Faecalibacterium | 0.0239 | 0.0286 | 0.004 | 0.0058 | <0.0001 | 0.17 |

Figure 12:
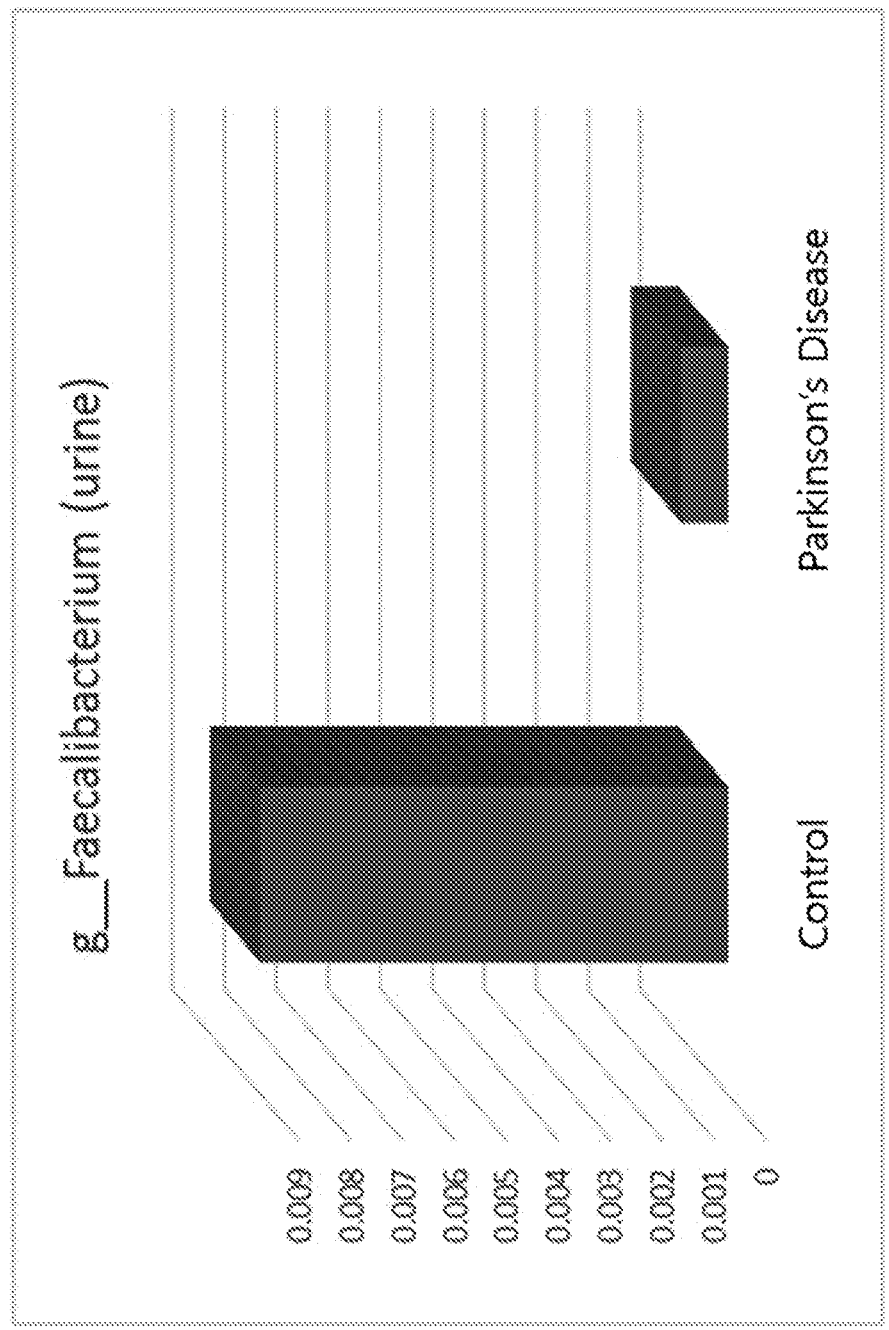
FIG. 12 is a result of comparing the distributions of vesicles derived from *Faecalibacterium prausnitzii* after metagenomic analysis of bacteria-derived vesicles present in the urine of Parkinson's disease patients and a normal individuals.

Example 13. Metagenomic Analysis of Bacteria-Derived Vesicles in Urine of Patient with Parkinson's Disease After a metagenomic analysis was performed using the method of Example 2 on the urine from 39 patients with Parkinson's disease, and 76 normal individuals who were matched in age and sex by extracting genes from vesicles present in the urine, the distribution of vesicles derived from *Faecalibacterium prausnitzii* was evaluated. As a result, it was confirmed that vesicles derived from *Faecalibacterium prausnitzii* were significantly decreased in the urine from the patients with Parkinson's disease as compared to the urine from the normal individuals (see Table 12 and FIG. 12).

TABLE 12

| | Urine | | | | | |
|---|---|---|---|---|---|---|
| | Control | | Parkinson's Disease | | t-test | |
| Taxon | Mean | SD | Mean | SD | p-value | Ratio |
| g_Faecalibacterium | 0.009 | 0.012 | 0.0009 | 0.0015 | <0.0001 | 0.10 |

Example 14. Isolation of *Faecalibacterium prausnitzii*-Derived Vesicles and Inflammation-Inducing Effect Based on the result of the above example, *Faecalibacterium prausnitzii* was isolated from a stool sample and cultured, followed by separation of vesicles. A *Faecalibacterium prausnitzii* strain was cultured in a brain heart infusion (BHI) medium until an absorbance (OD600) reached 1.0 to 1.5 in an anaerobic chamber at 37° C., and then sub-cultured. Afterward, a medium supernatant which does not contain the strain was collected, centrifuged at 10,000 g and 4° C. for 15 minutes, and filtered through a 0.45-µm filter. A supernatant obtained thereby was concentrated to a volume of 200 mL through ultrafiltration using a QuixStand benchtop system (GE Healthcare, UK) as a 100 kDa hollow filter membrane. Subsequently, the concentrated supernatant was filtered once again with a 0.22-µm filter and ultracentrifuged at 150,000 g and 4° C. for 3 hours, followed by suspension of a pellet in Dulbecco's Phosphate Buffered Saline (DPBS). Afterward, density gradient centrifugation was performed using 10%, 40% and 50% OptiPrep solutions (Axis-Shield PoC AS, Norway), and to prepare low-density solutions, the OptiPrep solutions were diluted with HEPES-buffered saline (20 mM HEPES, 150 mM NaCl, pH 7.4) before use. After centrifugation for 2 hours under conditions of 200,000 g and 4° C., each solution fractionated with an equal volume of 1 mL from the top layer was additionally ultracentrifuged for 3 hours under conditions of 150,000 g and 4° C. Afterward, a protein was quantified using a bicinchoninic acid (BCA) assay, and an experiment was performed on vesicles obtained as described above.

To examine the effect of the *Faecalibacterium prausnitzii*-derived vesicles on the secretion of inflammatory mediators from inflammatory cells, a mouse macrophage cell line, Raw 264.7 cells, was treated with *Faecalibacterium prausnitzii*-derived vesicles at various concentrations (0.1, 1, 10 µg/mL), and secretion amounts of inflammatory mediators (IL-6 and TNF-α) were measured. More specifically, the Raw 264.7 cells were seeded in a 24-well cell culture plate at $1\times10^5$ per well, and incubated in Dulbecco's Modified Eagle's Medium (DMEM) for 24 hours. Afterward, a culture supernatant was collected in a 1.5 mL tube, centrifuged at 3000 g for 5 minutes, thereby collecting a supernatant. The supernatant was stored at 4° C., followed by ELISA.

Figure 13A:
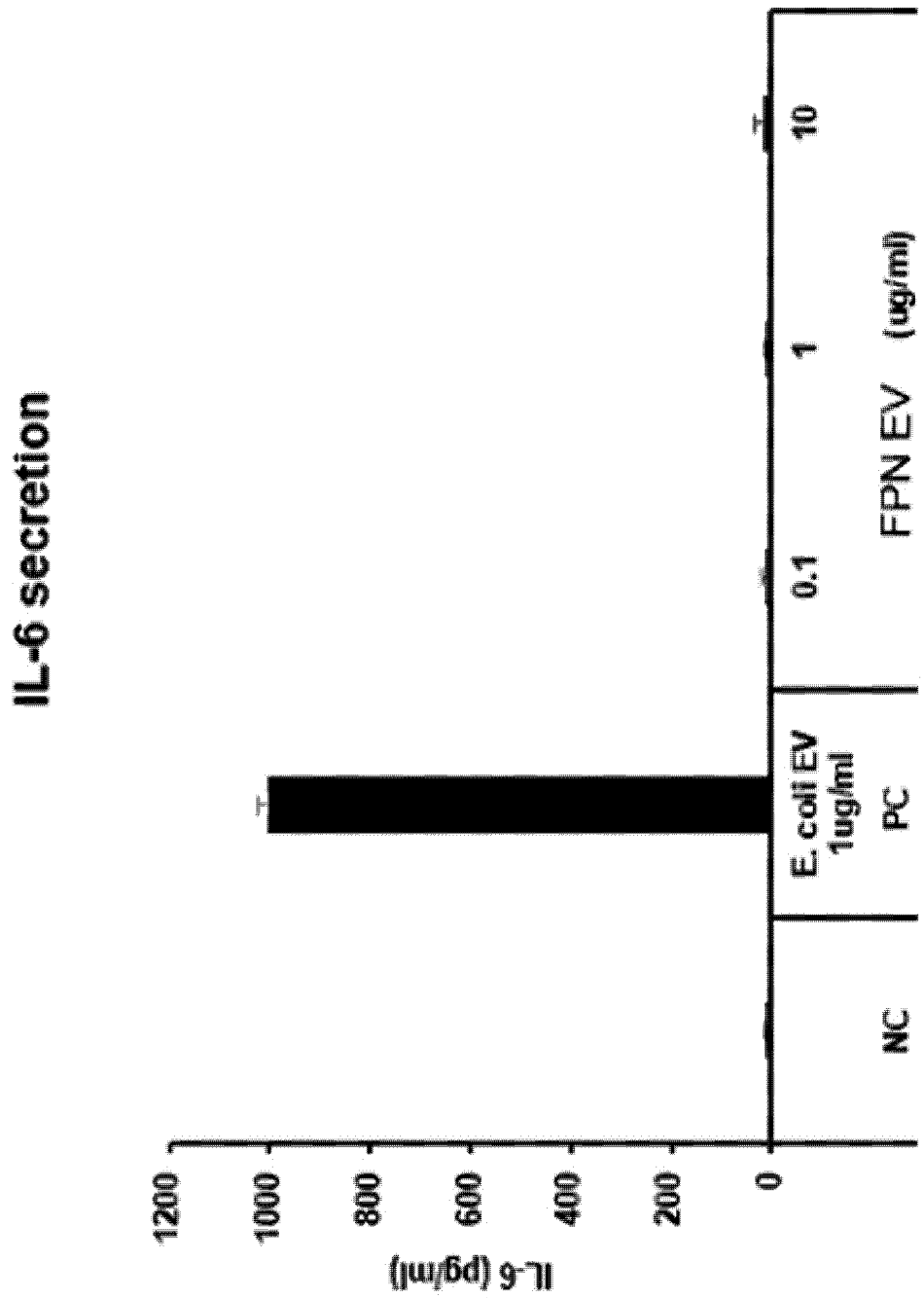
Figure 13B:
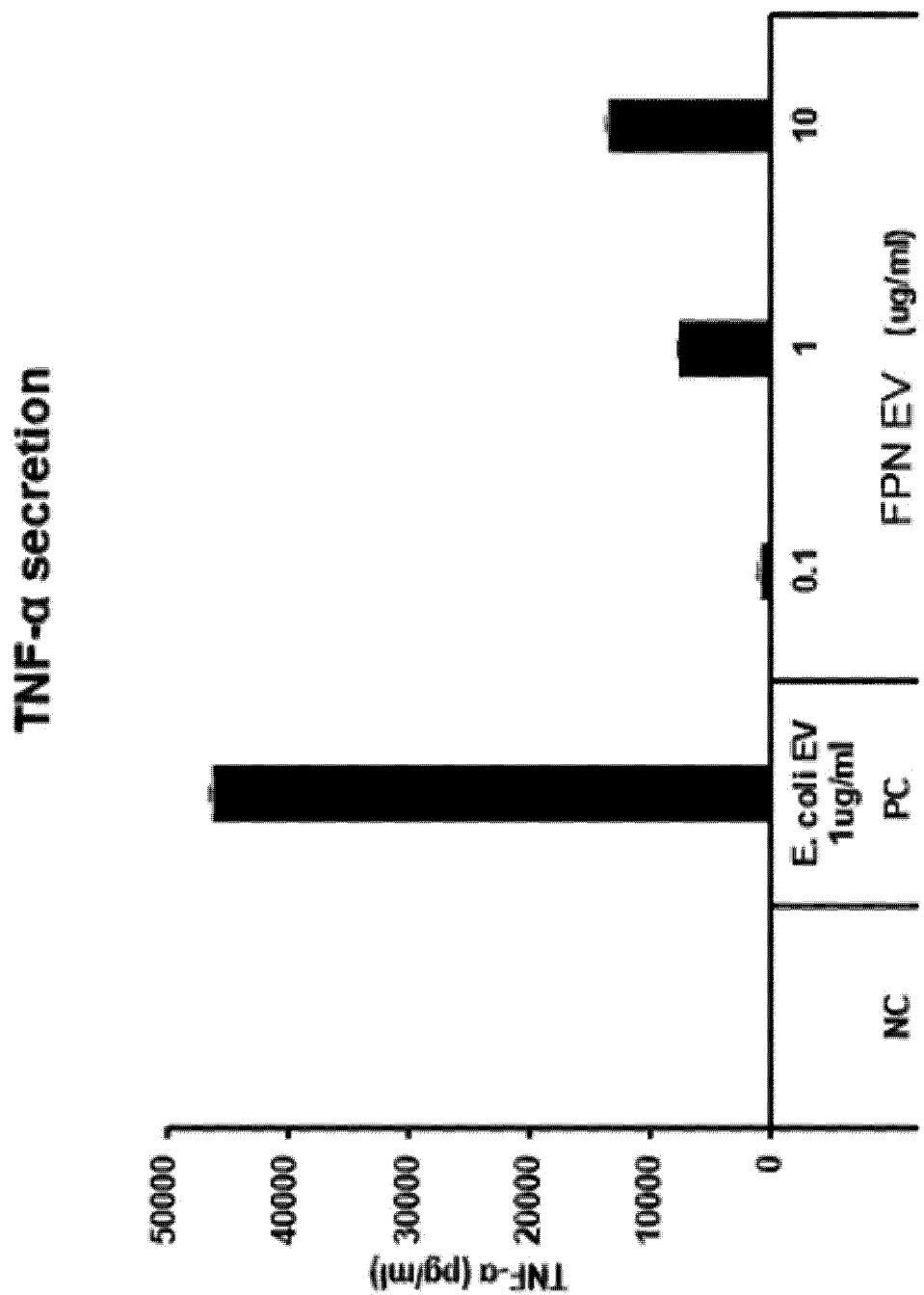

As a result, when *Faecalibacterium prausnitzii*-derived vesicles (FPN EVs) were pretreated, it was confirmed that the secretion of inflammatory mediators was significantly lower than the IL-6 and TNF-α secretion by *E. coli* EVs (refer to FIGS. 13A and 13B).

Example 15. Anti-Inflammatory Effects of *Faecalibacterium prausnitzii*-Derived Vesicles Based on the result of the above example, to investigate the anti-inflammatory effect of *Faecalibacterium prausnitzii*-derived vesicles on the secretion of inflammatory mediators by pathogenic vesicles in inflammatory cells, a mouse macrophage cell line, Raw 264.7 cells, was treated with *Faecalibacterium prausnitzii*-derived vesicles at various concentrations (0.1, 1 and 10 μg/mL), and then treated with pathogenic vesicles, which are involved in an inflammatory disease, *E. coli* EVs to measure secretion amounts of inflammatory mediators (IL-6 and TNF-α). More specifically, the Raw 264.7 cells were seeded in a 24-well cell culture plate at 1×10$^5$ per well, and then incubated in DMEM for 24 hours. Afterward, a culture supernatant was collected in a 1.5 ml tube and centrifuged at 3000 g for 5 minutes, thereby collecting a supernatant. The supernatant was stored at 4° C., followed by ELISA.

Figure 14A:
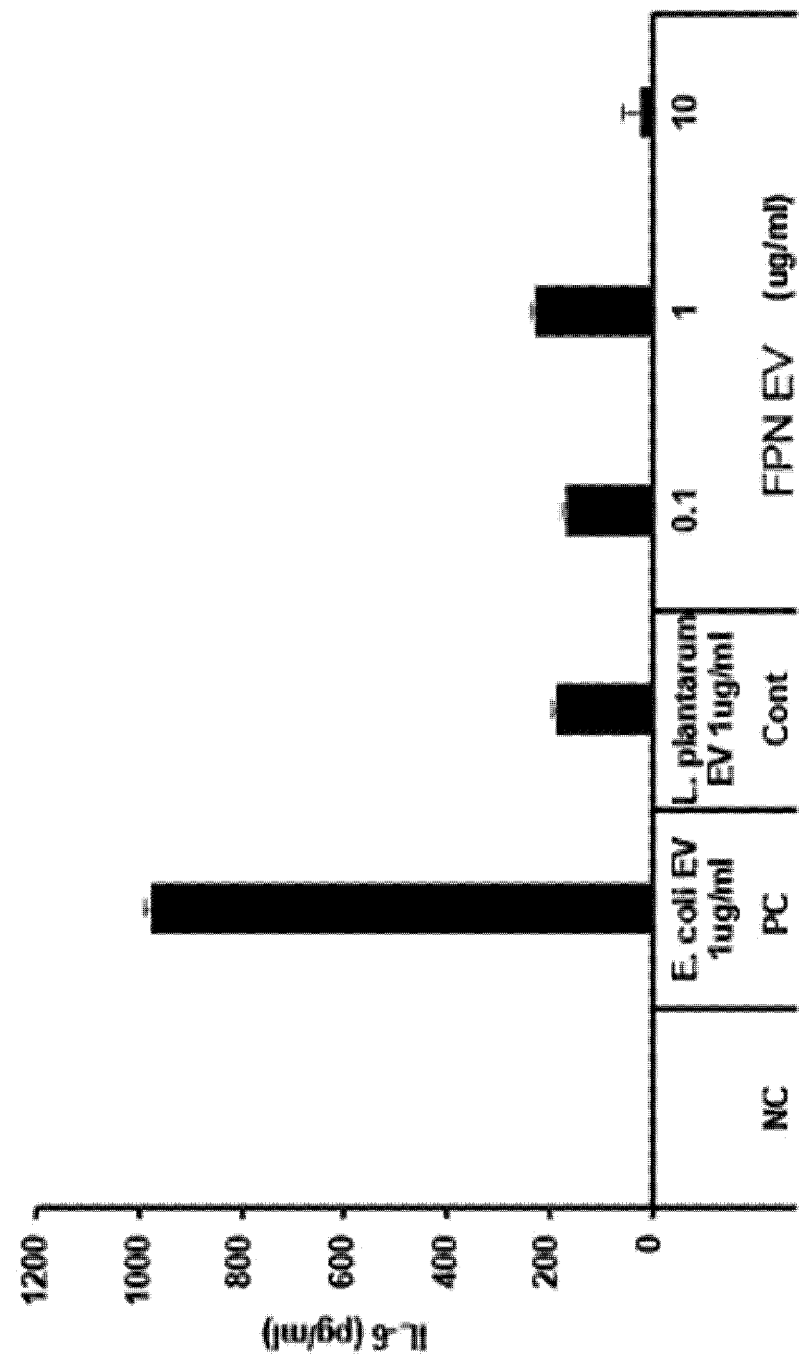
Figure 14B:
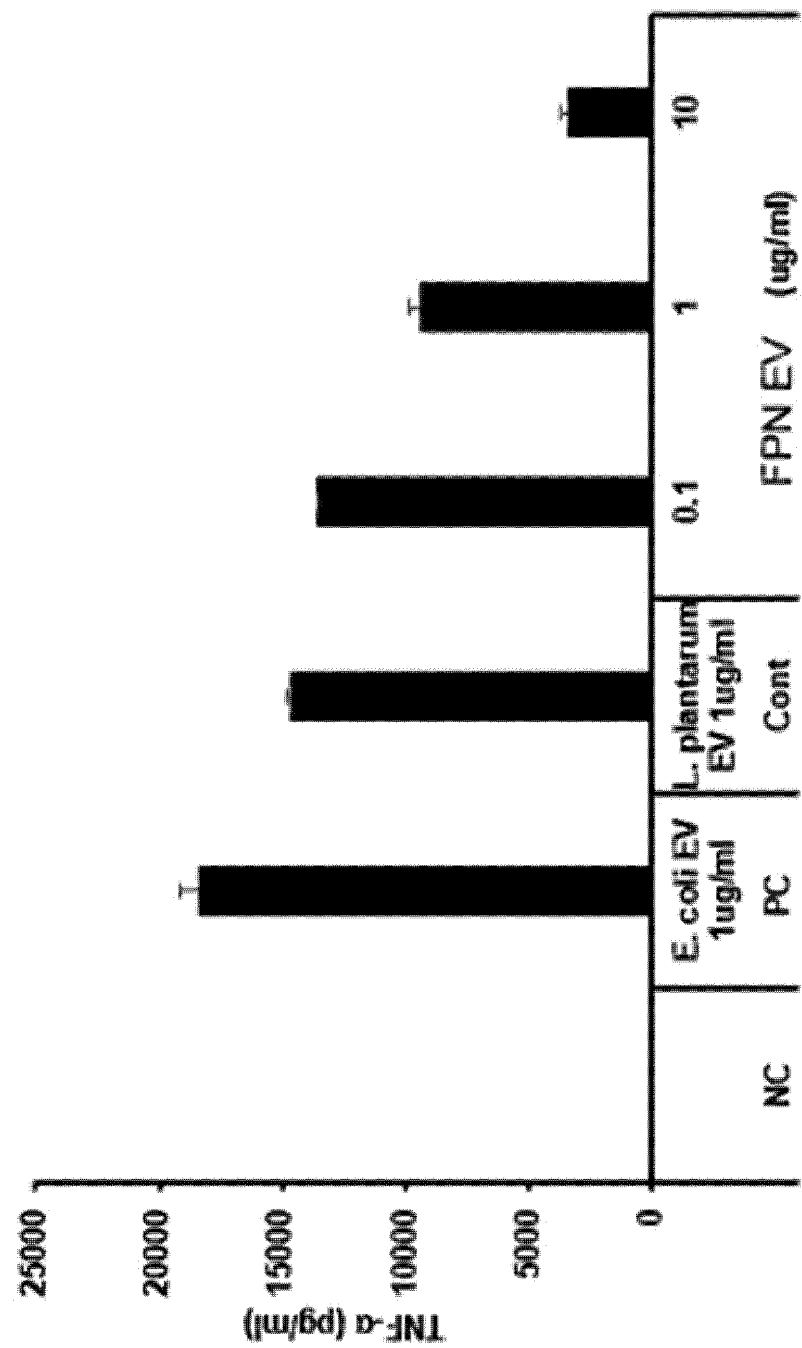

As a result, when the *Faecalibacterium prausnitzii*-derived vesicles (FPN EV) are pretreated, it was confirmed that the IL-6 and TNF-α secretion caused by *E. coli* EVs is significantly inhibited (refer to FIGS. 14A and 14B). This indicates that inflammation induced by a pathogenic causative factor such as *E. coli* EVs can be effectively inhibited by the *Faecalibacterium prausnitzii*-derived vesicles.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

Since the *Faecalibacterium prausnitzii*-derived vesicles according to the present invention may be used for a method of diagnosing gastric cancer, colorectal cancer, liver cancer, pancreatic cancer, cholangiocarcinoma, ovarian cancer, bladder cancer, lymphoma, myocardial infarction, atrial fibrillation or Parkinson's disease, and a food or drug composition for preventing, alleviating or treating the above-mentioned diseases, they are expected to be effectively used in the related pharmaceutical industry and food industry.

The invention claimed is:

1. A method of alleviating or treating inflammation, the method comprising administering to a subject in need thereof a composition consisting of an effective amount of an active ingredient and a pharmaceutically acceptable carrier,
   wherein the active ingredient is the vesicles derived from *Faecalibacterium prausnitzii*,
   wherein the bacteria of *Faecalibacterium prausnitzii* is removed in the composition, and
   wherein the vesicles inhibit secretion of IL-6 or TNF-α and thereby inhibit the inflammation.

2. The method of claim 1, wherein the composition is a pharmaceutical composition or a food composition.

3. The method of claim 1, wherein the vesicles have an average diameter of 10 to 200 nm.

4. The method of claim 1, wherein the vesicles are secreted naturally or artificially from *Faecalibacterium prausnitzii*.

* * * * *

```
                        SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S_V3_F
<220> FEATURE:
<221> NAME/KEY: misc_feature
<222> LOCATION: (42)
<223> OTHER INFORMATION: a or g or c or t/u

<400> SEQUENCE: 1
tcgtcggcag cgtcagatgt gtataagaga cagcctacgg gnggcwgcag              50

<210> SEQ ID NO 2
<211> LENGTH: 55
<212> TYPE: DNA
<213> ORGANISM: Artificial Sequence
<220> FEATURE:
<223> OTHER INFORMATION: 16S_V4_R

<400> SEQUENCE: 2
gtctcgtggg ctcggagatg tgtataagag acaggactac hvgggtatct aatcc         55
```